US005487969A

United States Patent [19]
Eberle et al.

[11] Patent Number: 5,487,969
[45] Date of Patent: Jan. 30, 1996

[54] METHOD OF DETECTION OF HERPES B VIRUS

[75] Inventors: Richard Eberle; Darla Black, both of Stillwater, Okla.; Franco Scinicariello; Julia Hilliard, both of San Antonio, Tex.

[73] Assignee: Southwest Foundation for Biomedical Research, San Antonio, Tex.

[21] Appl. No.: 42,747

[22] Filed: Apr. 1, 1993

[51] Int. Cl.$^6$ .................................................. C12Q 1/70
[52] U.S. Cl. ..................... 435/5; 536/23.72; 536/24.32; 536/24.33
[58] Field of Search ........................... 435/6, 5, 235.1; 536/23.72, 24.32, 24.33

[56] References Cited

PUBLICATIONS

Stratagene 1988 Catalog, pp. 69, and 76.
Bzik et al., Virology 155:322–333, 1986.
Hammerschmidt et al., Virology 165:388–405, 1988.
Wall, et al., Discrimination Between Twenty Isolates of Herpesvirus Simiae (B virus) by Restriction Enzyme Analysis of the Viral Genome, Virus Research, 12, pp. 283–296 (1989).
Sabin, et al., Acute Ascending Myelitis Following a Monkey Bite, With The Isolation of a Virus Capable of Reproducing the Disease, Journal of Experimental Med., vol. 59, pp. 115–136 (1934).
Ou, et al., DNA Amplification for Direct Detection of HIV–1 in DNA of Peripheral Blood Mononuclear Cells, Science, col. 239, pp. 295–297 (1987).
Saike, et al., Enzymatic Amplification of B–Globin Genomic Sequences and Restriction Site Analysis of Diagnosis of Sickle Cell Anemia, Science, vol. 230, pp. 1350–1354 (1985).
McCarthy, et al., A Review of Primate Herpes Viruses, Proc. Roy Soc., Med., vol. 68, pp. 145–150 (1975).
Fitzpatrick, et al., Mapping of 10 Epitopes on Bovien Herpesvirus Type 1 Glycoproteins gI and gIII Virology, 176, pp. 145–157 (1990).
Bzik, et al., Nucleotide Sequence Specifying the Glycoprotein Gene, gB, of Herpes Simplex Virus Type 1, Virology, 133, pp. 301–314 (1984).
Pierce, et al., B Virus, Its Current Significance, Am. J. Hyc., vol. 58, pp. 242–250 (1958).
Davidson, et al., B Virus Infection in Man, Ann. NY Acad, Sci., vol. 85, pp. 970–979 (1960).
Kebble, B Virus Infection in Monkeys, Ann. NY Acad. Sci., vol. 85, pp. 960–969 (1960).
Hilliard, et al., Herpesvirus Simiae (B Virus); Replication of the Virus and Identification of Viral Polypeptides in Infected Cells, Archives of Virology, 93, pp. 185–198 (1987).
Hilliard, et al., Simian Alphaherpesviruses and Their Relation to the Human Herpes Simplex Viruses, Archives of Virology, 109, pp. 83–102 (1989).
Eberle, et al., Relatedness of Glycoproteins Expressed on the Surface of Simian Herpes–Virus Virions and Infected Cells to Specific HSV Glycoproteins, Archives of Vir., 109, pp. 233–252 (1989).
Borchers, et al., Convserved Epitopes of Simian Herpesvirus SA8 and Bovine Herpesvirus Type 2, Archives of Virology, 111, pp. 1–14 (1990).
Rodu, et al., Simplified PCR–Based Detection and Typing Strategy for Human Papillamaviruses Utilizing a Single Oligonucleotide Primer Set, Biotechniques, 10, pp. 632–636 (1991).

(List continued on next page.)

*Primary Examiner*—W. Gary Jones
*Assistant Examiner*—Scott Houtteman
*Attorney, Agent, or Firm*—Cox & Smith Incorporated

[57] ABSTRACT

With the DNA sequence (SEQ ID NO:4:) of monkey B virus which codes for the gB glycoprotein (UL27) (SEQ ID NO:6:) and a portion (UL28) (SEQ ID NO:5:) of an ICP 18.5 kilodalton polypeptide (UL28), methods for early detection of the presence of monkey B virus in humans and monkeys can be performed by amplifying primer sequences and distinguishing the monkey B virus DNA coding for UL27 or UL28 from other herpes virus gB DNA using unique reaction conditions to permit unequivocal differentiation.

6 Claims, 1 Drawing Sheet

OTHER PUBLICATIONS

Vizoso, Recovery of Herpes Simiae (B Virus) From both Primary and Latent Infections in Rhesus Monkeys, Br. J. Exp. Path., 56, pp. 485–488 (1975).

Nagler, et al., A Fatal B. Virus Infection in a Person Subject to Recurrent Herpes Labialis, Canad M.A.J., vol. 79, pp. 743–745 (1958).

Barahona, et al., A Compendium of Herpesviruses Isolated from NonHuman Primates, Intervirology, 3, pp. 175–192 (1974).

Gary, et al., Comparative Complement Fixation and Serum Neutralization Antibody Titers to Herpes Simplex Virus Type 1 and Herpesvirus Simiae in Macaca Mulatta and Humans, Journal of Clinical Microbiology, vol. 5, No. 4, pp. 465–470 (1977).

Shibata, et al., Detection of Human Papilloma Virus in Paraffin–Embedded Tissue Using the Polymerase Chain Reaction, J. Exp. Med., vol. 167, pp. 225–230 (1988).

Desroriers, et al., Herpesvirus Tamarinus and Its Relation to Herpes Simplex Virus, J. Gen. Virol. 56, pp. 119–130 (1981).

Chase, et al., The Effect of Bovine Herpesvirus Type 1 Glycoproteins gI and gIII on Herpesvirus Infections, J. Gen. Virol., 70, pp. 1561–1569 (1989).

Fujinaga, et al., Simultaneous Detection and Typing of Genital Human Papillamavirus DNA using the Polymerase Chain Reaction, Journal of General Virology, 72, pp. 1039–1044 (1991).

Palmer, B Virus Herpesvirus Simiae: Historical Perspective, J. Med. Primatol, 16, pp. 99–130 (1987).

Dalgard, Herpesvirus Simiae Claims the LIfe of Primate Veterinarian, J. Med. Primatol, vol. 20 (1991).

Katz, et al., ELISA for Detection of Group–Common and Virus–Specific Antibodies in Human and Simian Sera Induced by Herpes Simplex and Related Simian Viruses, Journal of Virology Methods, 14, pp. 99–109 (1986).

Hilliard, et al., Rapid Identification of Herpesvirus Simiae (B Virus) DNA from Clinical Isolates in Non–Human Primate Colonies, Journal of Virological Methods, 13, pp. 55–62 (1986).

Eberle, et al., Replication of Simian Herpesvirus SA8 and Identification of Viral Polypeptides in Infected Cells, Journal of Virology, vol. 50, pp. 316–324 (1984).

Pellett, et al., Anatomy of the Herpes Simplex Virus 1 Strain F Glycoprotein B Gene: Primary Sequence and Predicted Protein Structure of the Wild Type and of Monoclonal Antibody–Resistance Mutants, Journal of Virology, vol. 53, pp. 243–253 (1985).

Stuve, et al., Structure and Expression of the Herpes Simplex Virus Type 2, Journal of Virology, vol. 61, pp. 326–335 (1987).

Drunken Littel, et al., Synthesis, Cellular Location, and Immunogencity of Bovine Herpesvirus 1 Glycoproteins gI and gIII Expressed by Recombiant Vaccinia Virus, Journal of Virology, vol. 63, pp. 2159–2168 (1989).

Horbal, et al., Continuous Epitopes of the Human Immunodeficiency Virus Type 1 (HIV–1) Transmembrance Glycoprotein and Reactivity of Human Sera to Synthetic Peptides Representing Various HIV–1 Isolates, Journal of Virology, vol. 65, pp. 2718–2723 (1991).

Powdrill, et al., Immunologic Priming with Recombinant Hepatitis A Virus Capside Proteins Produced in *Esherichia coli*, Journal of Virology, vol. 65, pp. 2686–2690 (1991).

Huang, et al., Localization of Immunogenic Domains in the Human Immunodeficiency Virus Type 2 Envelope, Journal of Virology, vol. 65, pp. 5073–5079 (1991).

Heberling, et al., A Dot–Immunobinding Assay on Nitrocellulose with Psoralen Inactive Herpesvirus simiae, Laboratory Animal Science, vol. 77, pp. 304–308 (1987).

Boulter, et al., A Comparison of Neutralization Tests for the Detection of Antibodies to Herpesvirus simiae (monkey B Virus), Laboratory Animal Science, pp. 150–152 (1982).

Zwartouw, et al., Transmission of B Virus Infection Between Monkeys Especially in Relation to Breeding Colonies, Laboratory Animals, 18, pp. 125–130 (1984).

Zwartouw, et al., Escretion of B Virus in Monkeys and Evidence of Genital Infection, Laboratory Animals, 18, pp. 65–70 (1984).

Rowley, et al., Rapid Detection of Herpes–Simplex–Virus DNA in Cerebrospinal Fluid of Patients with Herpes Simplex Encephalitis, The Lancelot, vol. 1, pp. 440–441 (1990).

Griffin, et al., B–Virus Infection in Humans—Pensacola, Fla., Epidemiologic Notes and Reports, vol. 35, No. 19, pp. 289–296 (1987).

Davenport, et al., B–Virus Infections in Humans—Michigan, Epidemiologic Notes and Reports, vol. 38, pp. 453–454 (1989).

METHOD OF DETECTION OF HERPES B VIRUS

The work leading to the present invention was partially supported by National Institutes of Health Grants Nos. P40 RR05162 and 401 RR03163. The U.S. Government may hold rights in the present patent.

FIELD OF THE INVENTION

This invention relates to a DNA segment (SEQ ID NO:4:) or a unique portion thereof from the monkey B virus which codes for gB glycoprotein (UL27) (SEQ ID NO:6:) and a portion (SEQ ID NO:5:) of an ICP 18.5 kilodalton polypeptide (UL28). The invention further relates to the use of this DNA segment (SEQ ID NO:4:) in, assays for detecting monkey B virus infection.

BACKGROUND OF THE INVENTION

At present, eight α-herpes viruses indigenous to primates are known. Several journal articles describing the Simian herpes viruses have been published (R. N. Hull, *The Simian Herpes Viruses in The Herpes Viruses* (D. S. Kaplan ed., Academic Press, 1973); K. McCarthy and F. A. Tosolini, *Proc. Roy. Soc. Med.*, 68:11–16 (1975)). Early studies using virus neutralization assays (Hull (1973)) and more recent molecular studies have demonstrated (R. C. Desrosiers and L. A. Folk, *J. Gen. Virol,.* 56:119–130 (1981); R. Eberle and J. K. Hilliard, *J. Virol.*, 50:316–324 (1984); Mou et al, *Arch. Virol.* 91:117–133 (1986); R. Eberle et al, *Arch. Virol.*, 109:233–252 (1989); J. K. Hilliard et al, *Arch. Virol.*, 109:83–102 (1989); K. Borchers et al, *Arch. Virol.*, 111:1–14 (1990)) that six of these viruses are closely related to each other. These are the two human herpes simplex viruses, HSV1 and HSV2; a virus indigenous to African monkeys, SA8 (herpes virus cercopithecus); monkey B virus (herpes virus simiae), which is indigenous in Asiatic macaques; herpes virus saimiri 1, which is indigenous in South American squirrel monkeys; and herpes virus ateles 1, which is indigenous in South American spider monkeys. In its natural host species, B virus causes self-limiting oral and genital lesions similar to those produced in humans by HSV1 and HSV2 (S. A. Keeble, *Ann. N.Y. Acad. Sci.*, 85:9960–9969 (1960); H. T. Zwartouw and E. A. Boulter, *Lab. Anim.*, 18:65–70 (1984); H. T. Zwartouw et al, *Lab. Anim.*, 18:125–130 (1984)). Humans can contract B virus by bites or scratches inflicted by macaques (W. L. Davidson and K. Hummeler, Ann. N.Y. *Acad. Sci.*, 85:970–979 (1960). In humans, untreated B virus infections are severe and usually fatal (A. B. Sabin and A. M. Wright, *J. Exp. Med.*, 59:115–136 (1934); S. P. Nagler and M. Klotz, *Canad. Med. Assoc. J.*, 79:743–745 (1958); E. C. Pierce et al, *Am. J. Hyg.*, 68:242–250 (1958); Centers for Disease Control, *MMWR*, 36:289–296 (1987); S. S. Kalter and R. L. Heberling, *Lab. Anim.*, 18:31–34 (1989). In recent cases of human B virus infection, experimental drug therapy has been effective at preventing mortality. However, the experimental nature of these drugs and the duration over which they must be used necessitates definitive B virus diagnosis prior to their use. The severe nature of B virus infections in humans has resulted in attempts, both past and ongoing, to establish B virus-free colonies of macaques for research use. Identification of B virus infected monkeys is an integral part of establishing such colonies.

B virus is closely related to both the human HSVs and to SA8 (J. K. Hilliard et al, *Arch. Virol.*, 93:185–198 (1987); Hilliard et al, (1989); Eberle et al, (1989)). Most humans have antibodies to HSV1 and/or HSV2, most adult macaques have antibodies to B virus, and most adult baboons have antibodies to SA8. Since antibodies to any one of these viruses will react with all four of these viruses, it is difficult to serologically diagnose the virus by which the antibodies were originally induced (i.e., the virus with which an individual is infected). Using sensitive and specialized assays, this can be done, albeit with considerable time, expertise, specialized biocontainment and expense (D. Katz et al, *J. Virol. Methods*, 14:99–109 (1986); R. Heberling and S. S. Kalter, *Lab. Anim. Sci.*, 37:304–308 (1987)). Similarly, currently employed techniques for identification of B virus or SA8 in clinical specimens requires not only the considerable time and expense associated with performing virus isolations but also additional testing to determine whether the virus isolated is HSV 1, HSV2, B virus, or SA8 (R. Eberle and D. Black, *Arch. Virol.*, 118:67–86 (1991); J. K. Hilliard et al, *J. Virol Methods*, 13:55–62 (1986)). In addition, there are strict regulations regarding the biosafety containment facilities necessary to work with biological samples suspected or known to contain B virus. This currently limits diagnostic activities for B virus in the United States to two laboratories.

B virus (Herpesvirus simiae) infection is an occupational hazard for monkey handlers and those who come into contact with macaque mucosal secretions and/or tissues, e.g., kidney cells frequently used for primary cell culture. Although B virus infections in humans are not common, the increased usage of macaque monkeys in biomedical research, especially AIDS research, has been associated with an increased frequency of human exposure to B virus with four fatalities in the past five years (Centers for Disease Control, *MMWR.*, 36:289–296 (1987); Centers for Disease Control, *MMWR.*, 38:353–354 (1989); *J. Med. Primatol.*, 20:373 (1991)).

B virus, an α-herpes virus, is enzootic in rhesus (Macaca mulatta), cynomolgus (Macaca fascicularis) and other Asiatic monkeys of the genus Macaca (A. E. Palmer, *J. Med. Primatol.*, 16:99–130 (1987)). It was first isolated in 1934 from a fatal human case following a bite from an apparently normal rhesus monkey (Sabin and Wright, (1934)). B virus is morphologically, biologically, and antigenically similar to herpes simplex virus types 1 and 2 (HSV1 and HSV2). Like HSV1 and HSV2 infections in humans, primary infection with B virus in macaques can result in gingivostomatitis, conjunctivitis or genital infections (Zwartouw and Boulter (1984)). Nonlesional, asymptomatic disease can also occur. Following primary infection, B virus can establish latency in the host and can reactivate spontaneously or in response to stress, resulting in shedding of virus in saliva and/or genital secretions even in the absence of visible lesions (A. D. Vizoso, *Br. J. Exp. Pathol.*, 56:485–488 (1975); E. A. Boulter, *J. Biol. Stand.*, 3:279–280 (1975)). In humans, B virus infection contracted by accidental monkey bite or from infected tissues or body fluids causes acute ascending myelitis, which leads to death from respiratory paralysis (Palmer (1987)). The recent outbreaks orb virus infection in humans, resulting in four fatalities including the demonstration of the first human to human B virus transmission, underscores the importance of rapid diagnosis of infection (CDC (1987); CDC (1989)). Rapid identification of infection permits early antiviral intervention reducing morbidity and mortality.

Currently, the diagnosis of B virus infection is accomplished primarily by isolation and identification of the virus. However, this method of detection requires strict biosafety containment facilities and specialized personnel. Given the high survival-value of antiviral treatments sufficiently early in the course of the disease, a rapid, specific and sensitive diagnostic test is needed. Polymerase chain reaction (PCR) technique (R. K. Saiki et al, *Science,* 230:1350–1354 (1985)), which allows the enzymatic amplification of minute quantities of DNA often undetectable by other methods, has been widely used for detection of several viral agents such as HSV (A. H. Rowley et al, *Lancet,* 335:440–441 (1990)), human immunodeficiency virus (HIV) (C-Y Ou et al, *Science,* 239:295–297 (1988)) and human papilloma viruses (HPV) (D. Shibata, *J. Exp. Med.,* 167:225–230 (1988)). The applicants herein use PCR for detection of B virus in human and monkey samples.

Concern about the occupational health hazards associated with handling monkeys infected with B virus, as well as other zoonotic infections, has led to a recognized need for B virus-free breeding colonies. The increased usage of macaques in biomedical research underscores the importance for rapid diagnosis of B virus infections. The recent human fatalities might each have been avoided by early diagnosis. To date, laboratory diagnosis of B virus infection has been achieved primarily by virus culture. After virus isolation in suitable cell lines, the identification of the virus is accomplished either by neutralization assay (G. W. Gary and E. L. Palmer, *J. Clin. Microbiol.,* 5:465–470 (1977)) or by molecular biology assays. Virus neutralization assays are cumbersome, time consuming and tedious. Furthermore, they often yield equivocal results. Using molecular biology assays, virus identification and differentiation can be performed by i) analysis of infected-cell polypeptides on SDS-polyacrylamide gels (Hilliard et al (1987)), or ii) restriction-endonuclease analysis of infected-cell DNA (Hilliard et al, *J. Virol. Methods,* 13:55–62 (1986); L. V. M. Wall et al, *Virus Res.,* 12:283–296 (1989)).

Such molecular biology assays for the purpose of diagnosis of monkey B virus infection can only be performed if the exact sequence of monkey B virus DNA and the proteins for which it codes are known and, furthermore, a method is devised for separating out and identifying the monkey B virus DNA and/or protein sequences from the infected cells. Before the present invention, the necessary sequence data and such a method for separating and identifying monkey B virus DNA from infected cells has not been known or obtainable.

SUMMARY OF THE INVENTION

The invention relates to a substantially pure form of a DNA segment (SEQ ID NO:4) of herpes simian monkey B virus coding for gB glycoprotein (UL27) (SEQ ID NO:6:) and a portion (SEQ ID NO:5:) of an ICP 18.5 kilodalton polypeptide (UL28), as well as some non-coding sequences. The invention further relates to a unique portion of this DNA segment.

The invention further relates to a protein (SEQ ID NO:6:) of gB glycoprotein (UL27) of herpes simian monkey B virus.

Additionally, the invention relates to a recombinant DNA molecule comprising a substantially pure DNA segment of herpes simian monkey B virus (SEQ ID NO:4:) and a vector for introducing the DNA segment into a host cell.

Furthermore, this invention relates to a method for detecting the presence of herpes simian monkey B virus in an individual comprising the steps of:

a) obtaining a tissue sample or a culture sample from an individual suspected of being infected with herpes simian monkey B virus;

b) extracting DNA from the tissue sample;

c) amplifying DNA segments from the extracted DNA, the DNA segments comprising at least a portion of a DNA segment (SEQ ID NO:4:) of herpes simian monkey B virus; and d) analyzing the amplified DNA segments to detect the presence of DNA sequences comprising at least a portion of the DNA segment (SEQ ID NO:4:).

Various other objects and advantages of the present invention will become apparent from the following figures and description of the invention.

Lane 1 contains the internal controls to assure that no DNA transfer contamination occurred during the PCR procedure. Lane 2 contains amplified Vero cell DNA as a negative control. Lane 3 contains B-virus strain (E2490). Lane 4 contains HSV-2 strain (186). Lane 5 contains HSV-1 strain (KOS). Lanes 6–9 contain B virus isolates from one infected human and three infected monkeys, respectively. The M represents the marker DNAs, on the left the Hae III digested φX174 RF DNA and on the right the φX174 Hinf I markers. The arrows indicate the size in base pairs. Only the amplified DNA of B virus isolates yielded two subfragments after Sac II-cleavage.

Figure 2:
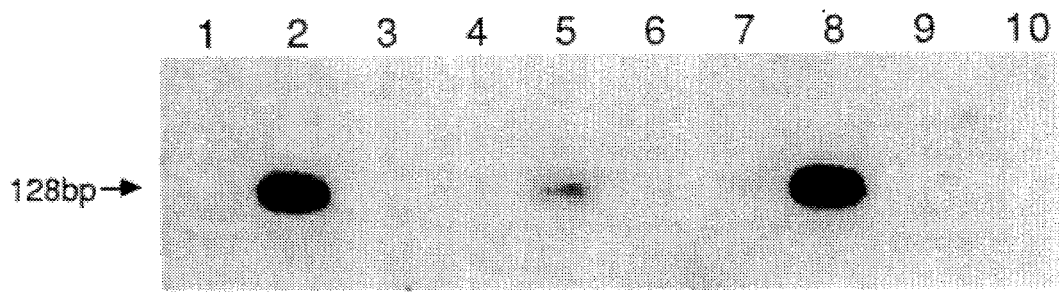

FIG. 2. Southern blot of PCR products of human sample DNA hybridized with oligonucleotide probe.

Lanes 1 and 4 are negative controls. Lanes 2, 3, 5, 6 and 7 are patient samples. Lane 8 is a B virus control. Lane 9 is HSV-1 control. Lane 10 is HSV-2 control.

DETAILED DESCRIPTION OF THE INVENTION

The DNA segment (SEQ ID NO:4:) of monkey B virus coding for the gB glycoprotein (UL27) (SEQ ID NO:6:) and a portion (SEQ ID NO:5:) of an ICP 18.5 kilodalton polypeptide (UL28)described here has been used as a basis for the development of differential diagnostic tests for rapid testing of suspect B virus cases. Comparison of the B virus gB proteins-glycoprotein sequence with sequences of gBs of other primate α-herpes viruses allows identification of regions which are strongly conserved among all of the primate α-herpes viruses and other regions which are highly divergent among them (Eberle, unpublished results). These observations together with the DNA sequences of the B virus (SEQ ID NO:4:), SA8 (SEQ ID NO:7:), HSV1 and HSV2 gB genes have been used to develop synthetic DNA primers BV1 (SEQ ID NO:1:) and BV2 (SEQ ID NO:2:) which are homologues to sequences of conserved regions and which flank a divergent region of the gene. These primers can be used in polymerase chain reactions (PCR) to amplify the flanking divergent region from any primate α-herpes virus DNA present in clinical or laboratory specimens. Knowing the DNA sequence of the divergent region of each of the four virus genes, the amplified product can then be further analyzed by determination of its size, restriction enzyme digestion pattern, or its DNA sequence to determine which of the four viruses it is derived from and hence which virus is present in the clinical specimen. A similar approach has been used by other investigators for detection and differential identification of various serotypes of papilloma viruses (Y. Fujinaga et al, *J. Gen. Virol.,* 72:1039–1044 (1991); B. Rodu et al, *Biotechniques,*

10:632–637 (1991)) but has not been applied to differential diagnosis of primate herpes viruses. Cloned or PCR-generated sequences derived from divergent (virus-specific) regions of the B virus gB gene sequence can also be utilized as virus-specific DNA probes for B virus, as they will hybridize with B virus DNA and not DNA of any of the other primate α-herpes viruses. Such a probe PB5 (SEQ ID NO:3:) which is specific for the B virus gB gene sequence is used in the present invention. Such probes also provide another approach for detection of B virus DNA in clinical and/or laboratory samples.

The amino acid sequences of the gB protein (UL27) (SEQ ID NO:6:) and a portion (SEQ ID NO:5:) of an ICP 18.5 kilodalton polypeptide (UL28) are generated by translating the sequence of the DNA segment (SEQ ID NO:4:). Knowing these amino acid sequences and the amino acid sequences of gB proteins of primate herpes viruses closely related to monkey B virus, such as SA8 gB protein sequence (SEQ ID NO: 8:) helps in analysis of which specific part of the monkey B virus DNA sequence should be used for design of DNA probes for the detection of monkey B virus DNA. In addition, the amino acid sequences themselves have immense potential use in the development of serological immunoassays which can specifically detect virus antigens and/or antibodies to B virus. One approach is to synthesize peptides which, based on the properties of the predicted amino acid sequence, are likely to be immunologically active. Such peptides can be used as substrate antigens in immunoassays to detect serum antibodies which recognize this specific peptide sequence (cf. M. L. Huang et al, *J. Virol.*, 65:5073–5079 (199 1); P. Horal et al, *J. Virol.*, 65:2718–2723 (1991)). Synthetic peptides are also commonly used to produce antibodies (cf. T. F. Powdrill and J. M. Johnston, *J. Virol.*, 65:2686–2690 (1991)) against specific regions of the gB protein which are unique to one virus (such as B virus or SA8). These antibodies can then be used to develop virus-specific immunoassays for differentiation of B virus from other primate α-herpes viruses and for identification of antibodies directed against B virus in primate serum samples. Knowing a DNA sequence of the coding and flanking non-coding sequences of a gene also permits the gene to be cloned into an expression vector to produce large quantities of the protein (C. C. L. Case et al, *J. Virol.*, 70:1561–1569 (1989); S. vanDrunen Littel-vandenHurk et al, *J. Virol.*, 63:2159–2168 (1989); D. A. R. Fitzpatrick et al, *Virol.*, 176:145–157 (1990)). This approach can also be used to produce large amounts of the B virus gB protein or portions of it for use in virus-specific immunoassays, thereby eliminating the hazards and biocontainment problems which arise when working with the infectious virus.

B virus DNA has been identified, using the methods of the present invention, in 16 out of 30 samples whereas only 11 of those 30 specimens were shown to be positive by virus isolation. This difference in results can be ascribed either to the low infectious virus titer present in the test specimens that could be a limiting factor in the viral culture isolation or to the advantage of the methods of the present invention in which the starting DNA template is amplified in the magnitude of $10^5$ to $10^7$ fold.

The methods of the present invention can also be used in the detection and control of B virus infections in macaque colonies. Identification of B virus shedding in infected macaques is an important step towards prevention of human B virus infections. These methods can be used as a reliable technique to monitor viral shedding in the absence of visible lesions in infected individuals, thus improving the understanding of the epidemiology and the pathogenesis of B virus infection. Furthermore, these methods can be a useful tool in the evaluation of antiviral drugs both in natural hosts and in B virus infected human patients receiving antiviral therapy.

B virus DNA from both human and monkey samples has been successfully detected using the methods of the present invention. The specificity of the primers BV1 (SEQ ID NO:1:) and BV2 (SEQ ID NO:2:) in the amplification of B virus DNA was demonstrated by Southern blot hybridization with an internal oligonucleotide probe PB5 (SEQ ID No:3:) and by digestion of PCR products with Sac II restriction enzyme. The specificity of sense primers B3 ((SEQ ID NO:9:) or (SEQ ID NO:11:)) and antisense primers B4 ((SEQ ID NO:10:) or B4' (SEQ ID NO:12:)) has also been demonstrated by digestion of PCR products with Hae III restriction enzyme.

Minor sequence variation is known to exist among different strains of a given virus, and such variation has been observed between DNA sequences of several HSV1 strains (E. J. Bzik, *Virol.*, 133:301–314 (1984); P. E. Pellett et al, *J. Virol.*, 53:243–253 (1985); L. L. Stuve et al, *J. Virol.*, 61:326–335 (1987)). By the same token, the use of sequences as primers which have minor sequence variations but are at least 90% homologous with selected sequences in the monkey B virus DNA segments (SEQ ID NO:4:) can also be effective as primers in applying the methods of the present invention to detect the presence of monkey B virus DNA in a sample.

EXAMPLES

Example 1

Viruses, cells and plasmids:

The E2490 strain of B virus, originally isolated from rhesus monkeys, was used. The virus was propagated and titered on CV-1 monkey kidney cells or Vero cells as described (R. Eberle and J. K. Hilliard (1984)). The pKBXX plasmid containing the HSV1 (KOS) gB gene coding sequences and 300–500 base pairs of 3' and 5' flanking sequences cloned into pBR322 (D. J. Bzik et al (1984) was kindly provided by Dr. S. Person (University of Pittsburgh Medical School).

Example 2

Recombinant DNA method:

B virus and SA8 DNA was purified from infected cells using the procedure of Walboomers and terSchagget (J. M. Walboomers, J.terSchagget (1976)). All cloning was done using the pUC19 (pLH1 and pBluescript® vectors) vector and recombinant plasmids were grown in DH5 α cells (BRL) using standard methods (T. Maniatis, E. F. Fritsch, J. Sambrook (1982)). Plasmid DNAs were isolated using an alkaline lysis miniprep method. Restriction fragments for subcloning were electroeluted from agarose gels (Molecular Biology Grade, BioRad Laboratories) prior to ligation with pUC 19. Hybridizations were performed at 60° C. for HSV1-SA8 hybridizations or at 80° C. for SA8-SA8 hybridizations (J. K. Hilliard, D. Black, R. Eberle (1989)).

Example 3

DNA sequencing:

Forward and reverse pUC primers were purchased from Promega Biotech and synthetic primers were purchased from National Biosciences, Inc. (Madison, Wis.). Samples were electrophoresed on 6–7.5% acrylamide/8M urea gels, dried, and autobiography performed using Kodak XAR-5 film.

The majority of the sequence data reported here was derived from sequencing of both strands. This included all areas in which there was significant divergence from the HSV sequence and all areas where repeated sequencing failed to give consistent results. The few areas where both strands were not sequenced were sequenced multiple times yielding consistent results and constituted conserved regions of the gB gene. The nucleotide sequence data reported in this paper have been deposited in the GenBank nucleotide sequence database (accession number M57388).

Example 4:

Sequence analysis:

DNA sequences were assembled and translated using the IBI Pustell programs (International Biotechnologies, Inc., New Haven, Conn). Alignments and secondary structural predictions for polypeptides were performed on a VAX 6320 at the Pittsburgh Supercomputing Center using the UWGCG programs. Multiple pairwise sequence comparisons and hierarchical cluster analysis were performed using the program MULTALIN of Corpet (F. Corpet (1988)).

Example 5

Viral DNA:

Viral stocks and viral DNA of B virus (strain E2490), HSV1 (strain KOS), and HSV2 (strain 186) were prepared as previously described (Hilliard et al (1986)). In addition, B virus strains isolated in the laboratory from an infected human and from three infected monkeys were used.

Example 7

Preparation of monkey samples

Samples from twelve B virus seropositive and three seronegative monkeys were used. Ocular, buccal or genital swabs were resuspended in one ml of Hank's modified essential medium. 100 μl aliquots of each sample were centrifuged and washed twine in PBS for cell collection. Each sample pellet was incubated for three hours at 55° C. in 100 μl of lysis buffer (50 mM Tris, 1 mM EDTA, 0.5% Tween 20) containing 400 μl/ml proteinase K. The samples were incubated at 95° C. for 10 minutes to inactivate the proteinase K and 30–50 μl of the supernatant was used for amplification.

Example 7

Preparation of human samples:

Swab samples from wounds or lesions of five humans working with macaque monkeys and from a B virus seropositive human in therapeutic treatment with acyclovir were processed as described above. DNAs from frozen autopsy samples collected following death of four humans from B virus infection were phenol-chloroform extracted followed by proteinase K digestion.

Example 8

PCR assay:

Two 21-base pair oligonucleotide primers, BV1 (SEQ ID NO:1::) and BV2 (SEQ ID NO:2:), were synthesized from a portion (SEQ ID NO:5:) of the ICP 18.5 (UL 28) gene of B virus (R. Eberle, D. Black, J. K. Hilliard, unpublished data). This primer set amplifies a 128 base pairs fragment of B virus and HSV1 and a 125 base pairs fragment of HSV2. The internal oligonucleotide probe (22 mer), PB5 (SEQ ID NO:3:) was selected for its B virus sequence specificity, having a 4 and 5 base pairs mismatch with the amplified HSV1 and the two primer DNA sequences (sense primer BV1(SEQ ID NO:1:) and antisense primer BV2(SEQ ID NO:2:)), respectively. The sequences of the primers and oligonucleotide probe are listed in Table 1. The sequences of the primers (sense primer B3 (SEQ ID NO:9:) or sense primer B3' (SEQ ID NO:11:)) and (antisense primer B4 ((SEQ ID NO:10:) or antisense primer B4' (SEQ ID NO: 12)) are also listed in Table 1.

TABLE 1

| | Oligonucleotide sequences of primers and probe to amplify B virus | |
|---|---|---|
| | Sequence | Orientation |
| BV1 (SEQ ID NO:1:) | 5' ACC TCA CGT ACG ACT CCG ACT 3' | Sense |
| BV2 (SEQ ID NO:2:) | 5' CTG CAG GAC CGA GTA GAG GAT 3' | Antisense |
| PB5 (SEQ ID NO:3:) | 5' GGA GAA GAC GTC GCG GTC GTA C 3' | Probe |
| B3 (SEQ ID NO:9:) | 5' TTC ACC GTG GCC TGG GAC TGG 3' | Sense |
| B3' (SEQ ID NO:11:) | 5' TTC ACC GTG GGC TGG GAC TGG 3' | Sense |
| B4 (SEQ ID NO:10:) | 5' GCG ATT CTG CAG CTC GCA CCA 3' | Antisense |
| B4' (SEQ ID NO:12:) | 5' GCG GTT CTG GAG CTC GCA CCA 3' | Antisense |

Amplification was carried out in a 100 μl reaction mixture containing 10 mmol/l Tris-HCl pH 8.3, 50 mmol/l KCl, 2 mmol MgCl$_2$, 200 μmol/l of each dNTP, 150 pmol of each primer and 2.5 units of Taq DNA polymerase (Perkin-Elmer Cetus). The reaction mix was covered with three drops of mineral oil and subjected, after an initial denaturation step at 94° C. for 5 minutes to 30 cycles of amplification using a DNA Thermal Cycler (Perkin-Elmer Cetus). Each cycle consisted of a denaturation step of the DNA template at 94° C. for 1 minute, primer-template annealing at 56° C. for 1 minute, and DNA synthesis at 72° C. for 1 minute. To prevent carryover of amplified DNA sequences, samples were prepared in a separate laboratory from that in which the reactions were performed. Since the barrel of pipetting devices can become contaminated with aerosols containing sample DNA, aerosol resistant tips (Continental Laboratory Products) were used. Moreover, internal controls that contained all the components of the reaction mixture except the template DNA were included in order to assess possible contamination during PCR preparation. These controls were assembled both during and after all other polymerase chain reactions had been set up.

Example 9

Analysis of PCR products:

For each sample, 20 μl of the amplified DNA product before or after digestion with Sac II restriction enzyme (Promega) was fractionated by 4% agarose gel electrophoresis (Nu Sieve 3:1, FMC), stained with ethidium bromide and transferred to a nylon membrane in alkaline buffer for Southern blot hybridization as recommended by the manufacturer (Schleicher & Schuell). The membrane was prehybridized at 42° C. for 1 hour in 5×SSC (1×SSC=0.15 mol/l sodium chloride, 0.015 mol/l sodium citrate), 5% Denhardt's solution (1×=0.02% bovine serum albumin, 0.02% Ficoll, 0.02% polyvinylpyrrolidone), 1% sodium dodecyl sulphate (SDS) and 100 μg/ml denatured salmon sperm DNA. Hybridization was carried out at 66° C. for 3 hours with an end-labeled-gamma-$^{32}$P-ATP oligonucleotide probe PB5 (SEQ. ID NO: 3:) in 5×SSC, 1% SDS and 100 μg/ml denatured salmon sperm DNA. The membranes were washed in 2×SSC, 1% SDS three times at room temperature for 10 minutes, then twice at 66° C. for 15 minutes in 1×SSC, 1% SDS and a final wash in 0.1×SSC, 1% SDS at 67° C. for 5 minutes. The membranes were then exposed to X-ray film (Kodak X-Omat) for 4–16 hours at –70° C.

Examples 10

Figure 1:
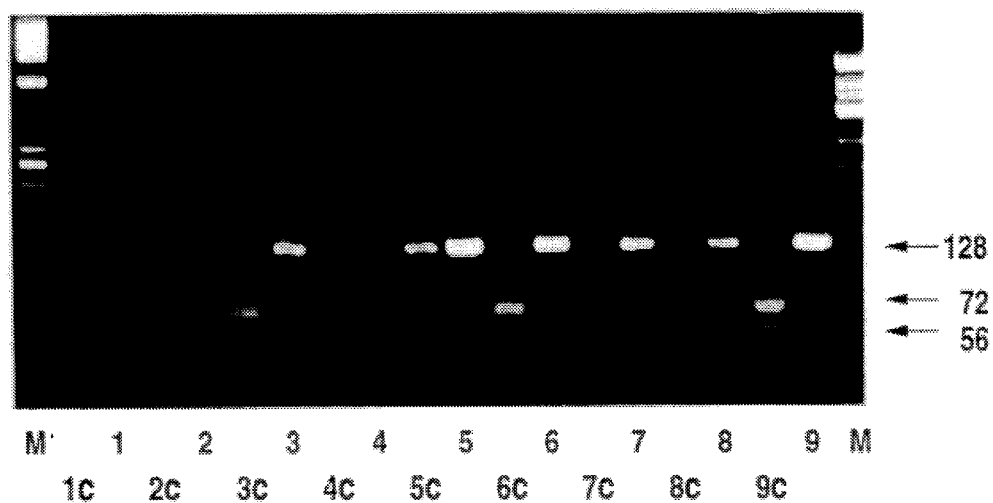
FIG. 1. Ethidium bromide-stained agarose gel analysis of undigested and SacII-cleaved marked c) PCR products.

Analysis of specificity of the PCR assay on control samples:

A fragment of about 128 base pairs of B virus, HSV 1 and HSV2 DNA was successfully amplified using the BV1 (SEQ ID NO:1:) and BV2 (SEQ ID NO:2:) primers. The ability of this set of primers to amplify the expected fragment was verified in four B virus isolates from three infected monkeys and one human B virus isolate. In order to unequivocally discriminate between DNA amplified from B virus versus HSV, the amplification product was analyzed by restriction enzyme analysis or by Southern blot hybridization using an end-labeled oligonucleotide internal probe specific for the amplified B virus DNA. Sac II was the restriction enzyme of choice since it does not cut the HSV 1 and HSV2 products while amplified B virus sequence should have a single cleavage site which will yield two fragments of about 72 and 56 base pairs, respectively. The Sac II pattern clearly distinguished different B virus isolates from both HSV types (FIG. 1). Hybridization of PCR products with the $^{32}$P-end-labeled oligonucleotide probe PB5 yielded a highly specific signal in B virus amplified products but no cross-hybridization with HSV1 or HSV2 amplified products (data not shown). In the case of the second primer set B3 ((SEQ ID NO:9:) or (SEQ ID NO:11:)) and B4 ((SEQ ID NO:10:) or (SEQ ID NO: 12:)), Hae III was used to differentiate the B virus PCR amplimer from those of HSV-1, HSV-2 and SA8.

Example 11

Human samples:

DNA extracted from frozen autopsy tissues of two B virus casualties and swab samples of the lesions from one B virus antibody positive and five suspect B virus infected humans were investigated by PCR followed by Southern blot hybridization. Southern blot hybridization of PCR products showed the presence of B virus in seven out of nine autopsy tissues investigated, whereas the swab samples investigated were negative (FIG. 2). However, one swab sample obtained from a buccal lesion of a monkey handler contained HSV related-nucleotide sequences as determined by ethidium bromide staining before and after Sac II restriction analysis. This was later confirmed by isolation of HSV1 from the swab sample. The PCR results were retrospectively compared with those for virus isolation. All the samples positive for B virus by culture were also positive by PCR. However, two samples were positive only by PCR, suggesting that the PCR assay is more sensitive.

Example 12

Monkey swab samples:

Of the 15 monkeys used in this study, 12 had B virus antibody titers by ELISA. Specimens obtained from 3 serologic negative monkeys were negative for B virus infection by PCR, as well as by virus culture. Swabs from 9 out of 12 antibody positive monkeys (primarily buccal swab specimens) were positive by PCR whereas only 6 were positive by virus culture.

While the foregoing invention has been described in some detail for purposes of clarity and understanding, it will be cleared to one skilled in the art from the reading of this disclosure that various changes in form and detail can be made without departing from the true scope of the invention.

What is claimed is:

1. A method for detecting the presence of herpes B virus in an individual, the method comprising the steps of:
   a) obtaining a tissue sample or a culture sample from an individual suspected of being infected with herpes B virus;
   b) extracting DNA from the tissue or culture sample;
   c) amplifying DNA segments from the extracted DNA by using a sense primer sequence consisting of BV1 (SEQ ID NO:1:) and an anti-sense primer sequence consisting of BV2 (SEQ ID NO:2:); and
   d) analyzing the amplified DNA segments to detect the presence of the DNA segment (SEQ ID NO:4:), the DNA segment (SEQ ID NO:4:) being detectable either by:
      i) digesting the amplified DNA segments with a restriction enzyme, said restriction enzyme being capable of digesting the DNA segment (SEQ ID NO:4:) but not capable of digesting HSV1 or HSV2; separating the digested segments by size; and detecting the presence or absence of digested segments; or
      ii) hybridizing the amplified DNA segments with labeled oligonucleotide probe consisting of PB5 (SEQ ID NO:3:) and detecting the presence or absence of hybridized segments;
wherein the presence of the DNA segment (SEQ ID NO:4:) indicates the presence of the virus.

2. The method according to claim 1, wherein the restriction enzyme is Sac II.

3. The method according to claim 1, wherein the oligonucleotide probe is labeled with a radioactive component.

4. A method for detecting the presence of herpes B virus in an individual, the method comprising the steps of:
   a) obtaining a tissue sample or a culture sample from an individual suspected of being infected with herpes B virus;
   b) extracting DNA from the tissue or culture sample;
   c) amplifying DNA segments from the extracted DNA by using a sense primer sequence consisting of B3 (SEQ ID NO:9:) or B3' (SEQ ID NO:11:) and an anti-sense primer sequence consisting of B4 (SEQ ID NO: 10:) or B4' (SEQ ID NO: 12:); and
   d) analyzing the amplified DNA segments to detect the presence of the DNA segment (SEQ ID NO:4:), the DNA segment (SEQ ID NO:4:) being detectable either by:
      i) digesting the amplified DNA segments with a restriction enzyme, said restriction enzyme being capable of digesting the DNA segment (SEQ ID NO:4:) but not capable of digesting HSV1 or HSV2; separating the digested segments by size; and detecting the presence or absence of digested segments; or
      ii) hybridizing the amplified DNA segments with labeled oligonucleotide probe consisting of PB5 (SEQ ID NO:3:) and detecting the presence or absence of hybridized segments;

wherein the presence of the DNA segment (SEQ ID NO:4:) indicates the presence of the virus.

5. The method according to claim 4 wherein the oligonucleotide probe is labeled with a radioactive component.

6. The method according to claim 4, wherein the restriction enzyme is Hae III.

* * * * *

UNITED STATES PATENT AND TRADEMARK OFFICE
CERTIFICATE OF CORRECTION

PATENT NO. : 5,487,969  
APPLICATION NO. : 08/042747  
DATED : January 30, 1996  
INVENTOR(S) : Richard Eberle et al.

Page 1 of 1

It is certified that error appears in the above-identified patent and that said Letters Patent is hereby corrected as shown below:

Column 1, Lines 4-7 omit

"The work leading to the present invention was partially supported by National Institutes of Health Grants Nos. P40 RR05162 and 401 RR03163. The U.S. Government may hold rights in the present patent."

replace with

"This invention was made with government support under Grant Numbers RR05162 and RR03163 awarded by the National Institutes of Health. The government has certain rights in the invention."

Signed and Sealed this
Second Day of October, 2012

David J. Kappos
*Director of the United States Patent and Trademark Office*

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: Genomic DNA ( x i ) SEQUENCE DESCRIPTION: SEQ ID NO:1:

ACCTCACGTA CGACTCCGAC T                                                    2 1

( 2 ) INFORMATION FOR SEQ ID NO:2:

( i ) SEQUENCE CHARACTERISTICS:

( A ) LENGTH: 21 base pairs
                    ( B ) TYPE: nucleic acid
                    ( C ) STRANDEDNESS: single
                    ( D ) TOPOLOGY: linear ( i i ) MOLECULE TYPE: Genomic DNA ( x i ) SEQUENCE DESCRIPTION: SEQ ID NO:2:

CTGCAGGACC GAGTAGAGGA T                                                                   21

( 2 ) INFORMATION FOR SEQ ID NO:3:

( i ) SEQUENCE CHARACTERISTICS:
                    ( A ) LENGTH: 22 base pairs
                    ( B ) TYPE: nucleic acid
                    ( C ) STRANDEDNESS: single
                    ( D ) TOPOLOGY: linear ( i i ) MOLECULE TYPE: Genomic DNA ( x i ) SEQUENCE DESCRIPTION: SEQ ID NO:3:

GGAGAAGACG TCGCGGTCGT AC                                                                  22

( 2 ) INFORMATION FOR SEQ ID NO:4:

( i ) SEQUENCE CHARACTERISTICS:
                    ( A ) LENGTH: 3177 base pairs
                    ( B ) TYPE: nucleic acid
                    ( C ) STRANDEDNESS: single
                    ( D ) TOPOLOGY: linear ( i i ) MOLECULE TYPE: Genomic DNA ( i x ) FEATURE:
                    ( A ) NAME/KEY: CDS
                    ( B ) LOCATION: 269..2941

( i x ) FEATURE:
                    ( A ) NAME/KEY: CDS
                    ( B ) LOCATION: 1..249

( x i ) SEQUENCE DESCRIPTION: SEQ ID NO:4:

```
AGT  CGA  GTG  GGG  CGG  CCC  GAC  TAC  GGT  CGG  CCC  ACC  CCC  GAG  GGG  GTC         48
Ser  Arg  Val  Gly  Arg  Pro  Asp  Tyr  Gly  Arg  Pro  Thr  Pro  Glu  Gly  Val
 1                   5                        10                       15

TAC  CGC  TAC  CCC  CCG  GGC  GTG  TAC  CTC  ACG  TAC  GAC  TCC  GAC  TGC  CCG         96
Tyr  Arg  Tyr  Pro  Pro  Gly  Val  Tyr  Leu  Thr  Tyr  Asp  Ser  Asp  Cys  Pro
                    20                       25                       30

CTG  GTG  GCC  ATC  GTC  GAG  TGC  GAG  CCG  GAC  GGC  GGC  ATC  GGC  CCG  CGG        144
Leu  Val  Ala  Ile  Val  Glu  Cys  Glu  Pro  Asp  Gly  Gly  Ile  Gly  Pro  Arg
               35                       40                       45

TCG  GTC  GTG  GTG  TAC  GAC  CGC  GAC  GTC  TTC  TCC  ATC  CTC  TAC  TCG  GTC        192
Ser  Val  Val  Val  Tyr  Asp  Arg  Asp  Val  Phe  Ser  Ile  Leu  Tyr  Ser  Val
          50                       55                       60

CTG  CAG  CAC  CTG  GCC  CCC  AGG  CTC  GCG  GCC  GGG  GGG  CCC  GAC  CAG  CCG        240
Leu  Gln  His  Leu  Ala  Pro  Arg  Leu  Ala  Ala  Gly  Gly  Pro  Asp  Gln  Pro
 65                      70                       75                       80

CCC  CCG  TAGCCGCCCG  CGCGCCGCGG  GG  ATG  CGG  CCC  CGC  GCC  GGC  CCC  CTC          292
Pro  Pro                              Met  Arg  Pro  Arg  Ala  Gly  Pro  Leu
                                       1                    5

CCC  CTC  CCC  TCC  CCC  CTC  GTC  CCC  CTC  CTG  GCC  CTC  GCC  CTC  CTC  GCC        340
Pro  Leu  Pro  Ser  Pro  Leu  Val  Pro  Leu  Leu  Ala  Leu  Ala  Leu  Leu  Ala
          10                       15                       20

GCG  ACC  CGG  CCG  CTG  GGC  CCC  GCG  GCG  GCG  ACC  CCC  GTG  GTG  AGC  CCG        388
Ala  Thr  Arg  Pro  Leu  Gly  Pro  Ala  Ala  Ala  Thr  Pro  Val  Val  Ser  Pro
 25                 30                        35                       40

CGG  GCC  TCT  CCG  GCC  CCG  CCC  GTC  CCC  GCG  GCC  ACG  CCG  ACG  TTT  CCA        436
```

| | | | | | | | | | | | | | | | | |
|---|---|---|---|---|---|---|---|---|---|---|---|---|---|---|---|---|
| Arg | Ala | Ser | Pro | Ala | Pro | Pro | Val | Pro | Ala | Ala | Thr | Pro | Thr | Phe | Pro | |
| | | | | 45 | | | | | 50 | | | | | 55 | | |

| GAT | GAC | GAT | AAC | GAT | GGC | GAG | GCC | GGG | GCC | GCG | CCG | GGC | GCG | CCG | GGC | 484 |
|---|---|---|---|---|---|---|---|---|---|---|---|---|---|---|---|---|
| Asp | Asp | Asp | Asn | Asp | Gly | Glu | Ala | Gly | Ala | Ala | Pro | Gly | Ala | Pro | Gly | |
| | | | 60 | | | | | 65 | | | | | 70 | | | |

| ACC | AAC | GCG | TCC | GTC | GAG | GCC | GGC | CAC | GCG | ACG | CTG | CGG | GAG | AAC | CTG | 532 |
|---|---|---|---|---|---|---|---|---|---|---|---|---|---|---|---|---|
| Thr | Asn | Ala | Ser | Val | Glu | Ala | Gly | His | Ala | Thr | Leu | Arg | Glu | Asn | Leu | |
| | | 75 | | | | | 80 | | | | | 85 | | | | |

| CGG | GAC | ATC | AAG | GCC | CTG | GAC | GGC | GAC | GCG | ACC | TTC | TAC | GTC | TGC | CCG | 580 |
|---|---|---|---|---|---|---|---|---|---|---|---|---|---|---|---|---|
| Arg | Asp | Ile | Lys | Ala | Leu | Asp | Gly | Asp | Ala | Thr | Phe | Tyr | Val | Cys | Pro | |
| | 90 | | | | 95 | | | | | 100 | | | | | | |

| CCG | CCG | ACC | GGC | GCC | ACG | GTG | GTG | CAG | TTT | GAG | CAG | CCC | CGG | CCG | TGC | 628 |
|---|---|---|---|---|---|---|---|---|---|---|---|---|---|---|---|---|
| Pro | Pro | Thr | Gly | Ala | Thr | Val | Val | Gln | Phe | Glu | Gln | Pro | Arg | Pro | Cys | |
| 105 | | | | | 110 | | | | | 115 | | | | | 120 | |

| CCG | CGG | GCG | CCC | CAC | GGC | CAG | AAC | TAC | ACC | GAG | GGG | ATC | GCG | GTG | ATC | 676 |
|---|---|---|---|---|---|---|---|---|---|---|---|---|---|---|---|---|
| Pro | Arg | Ala | Pro | His | Gly | Gln | Asn | Tyr | Thr | Glu | Gly | Ile | Ala | Val | Ile | |
| | | | | 125 | | | | | 130 | | | | | 135 | | |

| TTC | AAG | GAG | AAC | ATC | GCC | CCG | TAC | AAG | TTC | AAG | GCC | ACC | ATG | TAC | TAC | 724 |
|---|---|---|---|---|---|---|---|---|---|---|---|---|---|---|---|---|
| Phe | Lys | Glu | Asn | Ile | Ala | Pro | Tyr | Lys | Phe | Lys | Ala | Thr | Met | Tyr | Tyr | |
| | | | 140 | | | | | 145 | | | | | 150 | | | |

| AAG | GAC | GTG | ACC | GTC | TCG | CAG | GTC | TGG | TTC | GGC | CAC | AGG | TAC | TCG | CAG | 772 |
|---|---|---|---|---|---|---|---|---|---|---|---|---|---|---|---|---|
| Lys | Asp | Val | Thr | Val | Ser | Gln | Val | Trp | Phe | Gly | His | Arg | Tyr | Ser | Gln | |
| | | 155 | | | | | 160 | | | | | 165 | | | | |

| TTC | ATG | GGG | ATC | TTC | GAG | GAC | CGC | GCC | CCC | GTG | CCC | TTC | GAG | GAG | GTG | 820 |
|---|---|---|---|---|---|---|---|---|---|---|---|---|---|---|---|---|
| Phe | Met | Gly | Ile | Phe | Glu | Asp | Arg | Ala | Pro | Val | Pro | Phe | Glu | Glu | Val | |
| | 170 | | | | | 175 | | | | | 180 | | | | | |

| ATC | GAC | AAG | ATC | AAC | GCC | AGG | GGG | GTC | TGC | CGC | TCG | ACG | GCA | AAG | TAC | 868 |
|---|---|---|---|---|---|---|---|---|---|---|---|---|---|---|---|---|
| Ile | Asp | Lys | Ile | Asn | Ala | Arg | Gly | Val | Cys | Arg | Ser | Thr | Ala | Lys | Tyr | |
| 185 | | | | | 190 | | | | | 195 | | | | | 200 | |

| GTG | CGG | AAC | AAC | ATG | GAG | AGC | ACG | GCG | TTC | CAC | CGC | GAC | GAC | GAC | GAG | 916 |
|---|---|---|---|---|---|---|---|---|---|---|---|---|---|---|---|---|
| Val | Arg | Asn | Asn | Met | Glu | Ser | Thr | Ala | Phe | His | Arg | Asp | Asp | Asp | Glu | |
| | | | | 205 | | | | | 210 | | | | | 215 | | |

| TCG | GAC | ATG | AAG | CTG | AAG | CCC | GCG | AAG | GCC | GCG | ACC | CGC | ACC | AGC | CGC | 964 |
|---|---|---|---|---|---|---|---|---|---|---|---|---|---|---|---|---|
| Ser | Asp | Met | Lys | Leu | Lys | Pro | Ala | Lys | Ala | Ala | Thr | Arg | Thr | Ser | Arg | |
| | | | 220 | | | | | 225 | | | | | 230 | | | |

| GGC | TGG | CAC | ACC | ACC | GAC | CTG | AAG | TAC | AAC | CCC | TCG | CGG | ATC | GAG | GCG | 1012 |
|---|---|---|---|---|---|---|---|---|---|---|---|---|---|---|---|---|
| Gly | Trp | His | Thr | Thr | Asp | Leu | Lys | Tyr | Asn | Pro | Ser | Arg | Ile | Glu | Ala | |
| | | 235 | | | | | 240 | | | | | 245 | | | | |

| TTC | CAC | CGC | TAC | GGC | ACC | ACG | GTG | AAC | TGC | ATC | GTC | GAG | GAG | GTG | GAG | 1060 |
|---|---|---|---|---|---|---|---|---|---|---|---|---|---|---|---|---|
| Phe | His | Arg | Tyr | Gly | Thr | Thr | Val | Asn | Cys | Ile | Val | Glu | Glu | Val | Glu | |
| | 250 | | | | | 255 | | | | | 260 | | | | | |

| GCC | CGC | TCG | GTG | TAC | CCG | TAC | GAC | GAG | TTC | GTG | CTG | GCG | ACC | GGG | GAC | 1108 |
|---|---|---|---|---|---|---|---|---|---|---|---|---|---|---|---|---|
| Ala | Arg | Ser | Val | Tyr | Pro | Tyr | Asp | Glu | Phe | Val | Leu | Ala | Thr | Gly | Asp | |
| 265 | | | | | 270 | | | | | 275 | | | | | 280 | |

| TTT | GTG | TAC | ATG | TCG | CCG | TTC | TAC | GGC | TAC | CGC | GAC | GGG | GCC | CAC | GCC | 1156 |
|---|---|---|---|---|---|---|---|---|---|---|---|---|---|---|---|---|
| Phe | Val | Tyr | Met | Ser | Pro | Phe | Tyr | Gly | Tyr | Arg | Asp | Gly | Ala | His | Ala | |
| | | | | 285 | | | | | 290 | | | | | 295 | | |

| GAG | CAC | ACG | GCC | TAC | GCC | GCG | GAC | CGC | TTT | CGG | CAG | GTG | GAC | GGC | TAC | 1204 |
|---|---|---|---|---|---|---|---|---|---|---|---|---|---|---|---|---|
| Glu | His | Thr | Ala | Tyr | Ala | Ala | Asp | Arg | Phe | Arg | Gln | Val | Asp | Gly | Tyr | |
| | | | 300 | | | | | 305 | | | | | 310 | | | |

| TAC | GAG | CGC | GAC | CTC | TCC | ACG | GGG | CGG | CGC | GCC | TCC | ACG | CCG | GCG | ACG | 1252 |
|---|---|---|---|---|---|---|---|---|---|---|---|---|---|---|---|---|
| Tyr | Glu | Arg | Asp | Leu | Ser | Thr | Gly | Arg | Arg | Ala | Ser | Thr | Pro | Ala | Thr | |
| | | 315 | | | | | 320 | | | | | 325 | | | | |

| CGC | AAC | CTC | CTG | ACC | ACC | CCC | AAG | TTC | ACC | GTG | GGC | TGG | GAC | TGG | GCG | 1300 |
|---|---|---|---|---|---|---|---|---|---|---|---|---|---|---|---|---|
| Arg | Asn | Leu | Leu | Thr | Thr | Pro | Lys | Phe | Thr | Val | Gly | Trp | Asp | Trp | Ala | |
| | 330 | | | | | 335 | | | | | 340 | | | | | |

| CCC | AAG | CGC | CCC | TCG | GTC | TGC | ACG | CTG | ACC | AAG | TGG | CAG | GAG | GTG | GAC | 1348 |
|---|---|---|---|---|---|---|---|---|---|---|---|---|---|---|---|---|
| Pro | Lys | Arg | Pro | Ser | Val | Cys | Thr | Leu | Thr | Lys | Trp | Gln | Glu | Val | Asp | |
| 345 | | | | | 350 | | | | | 355 | | | | | 360 | |

| GAG | ATG | CTG | CGC | GCC | GAG | TAC | GGC | CCC | TCG | TTC | CGC | TTC | TCC | TCG | TCC | 1396 |
|---|---|---|---|---|---|---|---|---|---|---|---|---|---|---|---|---|

```
Glu  Met  Leu  Arg  Ala  Glu  Tyr  Gly  Pro  Ser  Phe  Arg  Phe  Ser  Ser  Ser
          365                      370                      375

GCC  CTC  TCC  ACC  ACC  TTC  ACG  ACC  AAC  CGC  ACC  GAG  TAC  GCC  CTG  TCG       1444
Ala  Leu  Ser  Thr  Thr  Phe  Thr  Thr  Asn  Arg  Thr  Glu  Tyr  Ala  Leu  Ser
               380                      385                      390

CGC  GTC  GAC  CTC  GGG  GAC  TGC  GTC  GGG  CGC  GAG  GCC  CGA  GAG  GCC  GTG       1492
Arg  Val  Asp  Leu  Gly  Asp  Cys  Val  Gly  Arg  Glu  Ala  Arg  Glu  Ala  Val
          395                      400                      405

GAC  CGC  ATC  TTC  CTC  CGG  CGC  TAC  AAC  GGC  ACG  CAC  GTG  AAG  GTG  GGC       1540
Asp  Arg  Ile  Phe  Leu  Arg  Arg  Tyr  Asn  Gly  Thr  His  Val  Lys  Val  Gly
     410                      415                      420

CAG  GTG  CAG  TAC  TAC  CTG  GCC  ACG  GCC  GGC  TTT  CTC  ATC  GCG  TAC  CAG       1588
Gln  Val  Gln  Tyr  Tyr  Leu  Ala  Thr  Ala  Gly  Phe  Leu  Ile  Ala  Tyr  Gln
425                      430                      435                      440

CCC  CTC  CTC  AGC  AAC  GGG  CTC  GTG  GAG  CTG  TAC  GTG  CGG  GAG  CTC  CTC       1636
Pro  Leu  Leu  Ser  Asn  Gly  Leu  Val  Glu  Leu  Tyr  Val  Arg  Glu  Leu  Leu
               445                      450                      455

CGC  GAG  CAG  GAG  GGC  CGG  CCG  GGC  GAC  GCG  GCG  GCG  ACC  CCG  AAG  CCC       1684
Arg  Glu  Gln  Glu  Gly  Arg  Pro  Gly  Asp  Ala  Ala  Ala  Thr  Pro  Lys  Pro
          460                      465                      470

TCC  GCC  GAC  CCC  CCC  GAC  GTG  GAG  CGC  ATC  AAG  ACC  ACG  TCC  TCG  GTC       1732
Ser  Ala  Asp  Pro  Pro  Asp  Val  Glu  Arg  Ile  Lys  Thr  Thr  Ser  Ser  Val
               475                      480                      485

GAG  TTC  GCG  CGC  CTG  CAG  TTC  ACG  TAC  GAC  CAC  ATC  CAG  CGG  CAC  GTC       1780
Glu  Phe  Ala  Arg  Leu  Gln  Phe  Thr  Tyr  Asp  His  Ile  Gln  Arg  His  Val
          490                      495                      500

AAC  GAC  ATG  CTG  GGG  CGC  ATC  GCC  ATC  GCC  TGG  TGT  GAG  CTC  CAG  AAC       1828
Asn  Asp  Met  Leu  Gly  Arg  Ile  Ala  Ile  Ala  Trp  Cys  Glu  Leu  Gln  Asn
505                      510                      515                      520

CAC  GAG  CTG  ACG  CTG  TGG  AAC  GAG  GCC  CGC  AAG  CTG  AAC  CCC  AAC  GCC       1876
His  Glu  Leu  Thr  Leu  Trp  Asn  Glu  Ala  Arg  Lys  Leu  Asn  Pro  Asn  Ala
               525                      530                      535

ATC  GCC  TCG  GCC  ACC  GTC  GGC  CGC  CGG  GTG  AGC  GCG  CGG  ATG  CTC  GGG       1924
Ile  Ala  Ser  Ala  Thr  Val  Gly  Arg  Arg  Val  Ser  Ala  Arg  Met  Leu  Gly
          540                      545                      550

GAC  GTG  ATG  GCC  GTC  TCC  ACC  TGC  GTG  CCC  GTG  ACC  CCC  GAC  AAC  GTC       1972
Asp  Val  Met  Ala  Val  Ser  Thr  Cys  Val  Pro  Val  Thr  Pro  Asp  Asn  Val
               555                      560                      565

ATC  ATG  CAG  AAC  TCG  ATG  CGC  GTC  CCC  GCG  CGC  CCC  GGG  ACG  TGC  TAC       2020
Ile  Met  Gln  Asn  Ser  Met  Arg  Val  Pro  Ala  Arg  Pro  Gly  Thr  Cys  Tyr
570                      575                      580

AGC  CGC  CCC  CTG  GTC  AGC  TTC  CGC  TAC  GAG  GAG  GGC  GGG  CCC  CTG  GTC       2068
Ser  Arg  Pro  Leu  Val  Ser  Phe  Arg  Tyr  Glu  Glu  Gly  Gly  Pro  Leu  Val
585                      590                      595                      600

GAG  GGC  CAG  CTG  GGC  GAG  GAC  AAC  GAG  ATC  CGC  CTC  GAG  CGC  GAC  GCC       2116
Glu  Gly  Gln  Leu  Gly  Glu  Asp  Asn  Glu  Ile  Arg  Leu  Glu  Arg  Asp  Ala
               605                      610                      615

CTC  GAG  CCC  TGC  ACC  GTC  GGT  CAC  CGG  CGC  TAC  TTC  ACC  TTC  GGG  GCG       2164
Leu  Glu  Pro  Cys  Thr  Val  Gly  His  Arg  Arg  Tyr  Phe  Thr  Phe  Gly  Ala
          620                      625                      630

GGC  TAC  GTG  TAC  TTT  GAG  GAT  TAC  GCG  TAC  TCC  CAC  CAG  CTG  GGT  CGC       2212
Gly  Tyr  Val  Tyr  Phe  Glu  Asp  Tyr  Ala  Tyr  Ser  His  Gln  Leu  Gly  Arg
               635                      640                      645

GCC  GAC  GTG  ACC  ACG  GTC  AGC  ACG  TTC  ATC  AAC  CTC  AAC  CTC  ACG  ATG       2260
Ala  Asp  Val  Thr  Thr  Val  Ser  Thr  Phe  Ile  Asn  Leu  Asn  Leu  Thr  Met
          650                      655                      660

CTC  GAG  GAC  CAC  GAG  TTC  GTG  CCC  CTG  GAG  GTC  TAC  ACC  CGC  CAG  GAG       2308
Leu  Glu  Asp  His  Glu  Phe  Val  Pro  Leu  Glu  Val  Tyr  Thr  Arg  Gln  Glu
665                      670                      675                      680

ATC  AAG  GAC  AGC  GGG  CTG  CTG  GAC  TAC  ACC  GAG  GTC  CAG  CGC  CGC  AAC       2356
```

| | | | | | | | | | | | | | | | | |
|---|---|---|---|---|---|---|---|---|---|---|---|---|---|---|---|---|
| Ile | Lys | Asp | Ser | Gly | Leu | Leu | Asp | Tyr | Thr | Glu | Val | Gln | Arg | Arg | Asn | |
| | | | | 685 | | | | | 690 | | | | | 695 | | |

| CAG | CTC | CAC | GCG | CTC | CGC | TTC | GCC | GAC | ATC | GAC | ACG | GTC | ATC | AAG | GCC | 2404 |
|---|---|---|---|---|---|---|---|---|---|---|---|---|---|---|---|---|
| Gln | Leu | His | Ala | Leu | Arg | Phe | Ala | Asp | Ile | Asp | Thr | Val | Ile | Lys | Ala | |
| | | | 700 | | | | | 705 | | | | | 710 | | | |

| GAC | GCG | CAC | GCG | CCG | CTG | TTC | GCG | GGC | CTC | TAC | TCC | TTC | TTC | GAG | GGC | 2452 |
|---|---|---|---|---|---|---|---|---|---|---|---|---|---|---|---|---|
| Asp | Ala | His | Ala | Pro | Leu | Phe | Ala | Gly | Leu | Tyr | Ser | Phe | Phe | Glu | Gly | |
| | | 715 | | | | | 720 | | | | | 725 | | | | |

| CTC | GGG | GAC | GTG | GGC | CGC | GCG | GTC | GGC | AAG | GTC | GTC | ATG | GGC | ATC | GTG | 2500 |
|---|---|---|---|---|---|---|---|---|---|---|---|---|---|---|---|---|
| Leu | Gly | Asp | Val | Gly | Arg | Ala | Val | Gly | Lys | Val | Val | Met | Gly | Ile | Val | |
| | 730 | | | | | 735 | | | | | 740 | | | | | |

| GGG | GGC | GTC | GTC | TCC | GCC | GTC | TCG | GGC | GTG | TCC | TCC | TTC | CTC | TCC | AAC | 2548 |
|---|---|---|---|---|---|---|---|---|---|---|---|---|---|---|---|---|
| Gly | Gly | Val | Val | Ser | Ala | Val | Ser | Gly | Val | Ser | Ser | Phe | Leu | Ser | Asn | |
| 745 | | | | | 750 | | | | | 755 | | | | | 760 | |

| CCC | TTC | GGG | GCC | CTG | GCC | GTC | GGG | CTG | CTG | GTC | CTG | GCC | GGG | CTG | GCG | 2596 |
|---|---|---|---|---|---|---|---|---|---|---|---|---|---|---|---|---|
| Pro | Phe | Gly | Ala | Leu | Ala | Val | Gly | Leu | Leu | Val | Leu | Ala | Gly | Leu | Ala | |
| | | | | 765 | | | | | 770 | | | | | 775 | | |

| GCG | GCC | TTC | TTC | GCC | TTC | CGC | TAC | GTC | ATG | CGC | CTG | CAG | CGC | AAC | CCC | 2644 |
|---|---|---|---|---|---|---|---|---|---|---|---|---|---|---|---|---|
| Ala | Ala | Phe | Phe | Ala | Phe | Arg | Tyr | Val | Met | Arg | Leu | Gln | Arg | Asn | Pro | |
| | | | 780 | | | | | 785 | | | | | 790 | | | |

| ATG | AAG | GCC | CTG | TAC | CCG | CTG | ACC | ACC | AAG | GAG | CTC | AAG | AGC | GAC | GGG | 2692 |
|---|---|---|---|---|---|---|---|---|---|---|---|---|---|---|---|---|
| Met | Lys | Ala | Leu | Tyr | Pro | Leu | Thr | Thr | Lys | Glu | Leu | Lys | Ser | Asp | Gly | |
| | | 795 | | | | | 800 | | | | | 805 | | | | |

| CCG | TCG | CGC | GGC | GAC | GGC | GGG | GAC | GGC | GCC | TCC | GGG | GGC | GGC | GAG | GAG | 2740 |
|---|---|---|---|---|---|---|---|---|---|---|---|---|---|---|---|---|
| Pro | Ser | Arg | Gly | Asp | Gly | Gly | Asp | Gly | Ala | Ser | Gly | Gly | Gly | Glu | Glu | |
| 810 | | | | | 815 | | | | | 820 | | | | | | |

| GAC | TTC | GAC | GAG | GCC | AAG | CTG | GCG | CAG | GCG | CGG | GAG | ATG | ATA | CGC | TAC | 2788 |
|---|---|---|---|---|---|---|---|---|---|---|---|---|---|---|---|---|
| Asp | Phe | Asp | Glu | Ala | Lys | Leu | Ala | Gln | Ala | Arg | Glu | Met | Ile | Arg | Tyr | |
| 825 | | | | | 830 | | | | | 835 | | | | | 840 | |

| ATG | GCC | CTG | GTG | TCG | GCC | ATG | GAG | CGC | ACG | GAG | CAC | AAG | GCC | CGC | AAG | 2836 |
|---|---|---|---|---|---|---|---|---|---|---|---|---|---|---|---|---|
| Met | Ala | Leu | Val | Ser | Ala | Met | Glu | Arg | Thr | Glu | His | Lys | Ala | Arg | Lys | |
| | | | | 845 | | | | | 850 | | | | | 855 | | |

| AAG | GGC | ACG | AGC | GCC | CTG | CTG | AGC | GCC | AAG | GTC | ACC | AAC | ATG | GTG | ATG | 2884 |
|---|---|---|---|---|---|---|---|---|---|---|---|---|---|---|---|---|
| Lys | Gly | Thr | Ser | Ala | Leu | Leu | Ser | Ala | Lys | Val | Thr | Asn | Met | Val | Met | |
| | | | 860 | | | | | 865 | | | | | 870 | | | |

| CGA | AAG | CGC | GCC | AAG | CCG | CGG | TAC | TCC | CCC | CTG | GGC | GAC | ACA | GAC | GAA | 2932 |
|---|---|---|---|---|---|---|---|---|---|---|---|---|---|---|---|---|
| Arg | Lys | Arg | Ala | Lys | Pro | Arg | Tyr | Ser | Pro | Leu | Gly | Asp | Thr | Asp | Glu | |
| | | 875 | | | | | 880 | | | | | 885 | | | | |

| GAG | GAG | CTA | TAGCACCCCC | GGGGGCCGAG | GCCCGCGTGT | CCGCCACGGC | 2981 |
|---|---|---|---|---|---|---|---|
| Glu | Glu | Leu | | | | | |
| | | 890 | | | | | |

| CGTGCGCGAC | GGGCGTTTGT | TCGGTTAATA | AAAAAGTAAT | TAATCACATT | CCGTTGTGGA | 3041 |
|---|---|---|---|---|---|---|
| GGTCTGTTCT | CGGCTCTTGG | GGTGCGCGTG | CGCGGTCCCG | TTTCCTCCCC | CCTCACCCTC | 3101 |
| CTTCCACTCA | CTGCAACTTT | TGGAAATAGT | CGGCTGGGGC | GAAATTCGCC | CGCCGCCCGG | 3161 |
| CCTGTGGGTC | CGGGTG | | | | | 3177 |

( 2 ) INFORMATION FOR SEQ ID NO:5:

( i ) SEQUENCE CHARACTERISTICS:
        ( A ) LENGTH: 82 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| Ser | Arg | Val | Gly | Arg | Pro | Asp | Tyr | Gly | Arg | Pro | Thr | Pro | Glu | Gly | Val |
|---|---|---|---|---|---|---|---|---|---|---|---|---|---|---|---|
| 1 | | | | 5 | | | | | 10 | | | | | 15 | |

| Tyr | Arg | Tyr | Pro | Pro | Gly | Val | Tyr | Leu | Thr | Tyr | Asp | Ser | Asp | Cys | Pro |
|---|---|---|---|---|---|---|---|---|---|---|---|---|---|---|---|
| | | | 20 | | | | | 25 | | | | | 30 | | |

-continued

| | | | | | | | | | | | | | | |
|---|---|---|---|---|---|---|---|---|---|---|---|---|---|---|
| Leu | Val | Ala | Ile | Val | Glu | Cys | Glu | Pro | Asp | Gly | Gly | Ile | Gly | Pro | Arg |
| | | 35 | | | | 40 | | | | | 45 | | | |
| Ser | Val | Val | Val | Tyr | Asp | Arg | Asp | Val | Phe | Ser | Ile | Leu | Tyr | Ser | Val |
| | 50 | | | | 55 | | | | | 60 | | | | |
| Leu | Gln | His | Leu | Ala | Pro | Arg | Leu | Ala | Ala | Gly | Gly | Pro | Asp | Gln | Pro |
| 65 | | | | 70 | | | | | 75 | | | | | 80 |
| Pro | Pro | | | | | | | | | | | | | | |

( 2 ) INFORMATION FOR SEQ ID NO:6:

( i ) SEQUENCE CHARACTERISTICS:
        ( A ) LENGTH: 891 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | | |
|---|---|---|---|---|---|---|---|---|---|---|---|---|---|---|---|
| Met | Arg | Pro | Arg | Ala | Gly | Pro | Leu | Pro | Leu | Pro | Ser | Pro | Leu | Val | Pro |
| 1 | | | | 5 | | | | | 10 | | | | | 15 | |
| Leu | Leu | Ala | Leu | Ala | Leu | Leu | Ala | Ala | Thr | Arg | Pro | Leu | Gly | Pro | Ala |
| | | | 20 | | | | | 25 | | | | | 30 | | |
| Ala | Ala | Thr | Pro | Val | Val | Ser | Pro | Arg | Ala | Ser | Pro | Ala | Pro | Pro | Val |
| | | 35 | | | | | 40 | | | | | 45 | | | |
| Pro | Ala | Ala | Thr | Pro | Thr | Phe | Pro | Asp | Asp | Asp | Asn | Asp | Gly | Glu | Ala |
| | 50 | | | | | 55 | | | | | 60 | | | | |
| Gly | Ala | Ala | Pro | Gly | Ala | Pro | Gly | Thr | Asn | Ala | Ser | Val | Glu | Ala | Gly |
| 65 | | | | | 70 | | | | | 75 | | | | | 80 |
| His | Ala | Thr | Leu | Arg | Glu | Asn | Leu | Arg | Asp | Ile | Lys | Ala | Leu | Asp | Gly |
| | | | | 85 | | | | | 90 | | | | | 95 | |
| Asp | Ala | Thr | Phe | Tyr | Val | Cys | Pro | Pro | Pro | Thr | Gly | Ala | Thr | Val | Val |
| | | | 100 | | | | | 105 | | | | | 110 | | |
| Gln | Phe | Glu | Gln | Pro | Arg | Pro | Cys | Pro | Arg | Ala | Pro | His | Gly | Gln | Asn |
| | | 115 | | | | | 120 | | | | | 125 | | | |
| Tyr | Thr | Glu | Gly | Ile | Ala | Val | Ile | Phe | Lys | Glu | Asn | Ile | Ala | Pro | Tyr |
| | 130 | | | | | 135 | | | | | 140 | | | | |
| Lys | Phe | Lys | Ala | Thr | Met | Tyr | Tyr | Lys | Asp | Val | Thr | Val | Ser | Gln | Val |
| 145 | | | | | 150 | | | | | 155 | | | | | 160 |
| Trp | Phe | Gly | His | Arg | Tyr | Ser | Gln | Phe | Met | Gly | Ile | Phe | Glu | Asp | Arg |
| | | | | 165 | | | | | 170 | | | | | 175 | |
| Ala | Pro | Val | Pro | Phe | Glu | Glu | Val | Ile | Asp | Lys | Ile | Asn | Ala | Arg | Gly |
| | | | 180 | | | | | 185 | | | | | 190 | | |
| Val | Cys | Arg | Ser | Thr | Ala | Lys | Tyr | Val | Arg | Asn | Asn | Met | Glu | Ser | Thr |
| | | 195 | | | | | 200 | | | | | 205 | | | |
| Ala | Phe | His | Arg | Asp | Asp | Asp | Glu | Ser | Asp | Met | Lys | Leu | Lys | Pro | Ala |
| | 210 | | | | | 215 | | | | | 220 | | | | |
| Lys | Ala | Ala | Thr | Arg | Thr | Ser | Arg | Gly | Trp | His | Thr | Thr | Asp | Leu | Lys |
| 225 | | | | | 230 | | | | | 235 | | | | | 240 |
| Tyr | Asn | Pro | Ser | Arg | Ile | Glu | Ala | Phe | His | Arg | Tyr | Gly | Thr | Thr | Val |
| | | | | 245 | | | | | 250 | | | | | 255 | |
| Asn | Cys | Ile | Val | Glu | Glu | Val | Glu | Ala | Arg | Ser | Val | Tyr | Pro | Tyr | Asp |
| | | | 260 | | | | | 265 | | | | | 270 | | |
| Glu | Phe | Val | Leu | Ala | Thr | Gly | Asp | Phe | Val | Tyr | Met | Ser | Pro | Phe | Tyr |
| | | 275 | | | | | 280 | | | | | 285 | | | |
| Gly | Tyr | Arg | Asp | Gly | Ala | His | Ala | Glu | His | Thr | Ala | Tyr | Ala | Ala | Asp |
| | 290 | | | | | 295 | | | | | 300 | | | | |

```
Arg  Phe  Arg  Gln  Val  Asp  Gly  Tyr  Tyr  Glu  Arg  Asp  Leu  Ser  Thr  Gly
305                 310                      315                      320

Arg  Arg  Ala  Ser  Thr  Pro  Ala  Thr  Arg  Asn  Leu  Leu  Thr  Thr  Pro  Lys
                    325                      330                      335

Phe  Thr  Val  Gly  Trp  Asp  Trp  Ala  Pro  Lys  Arg  Pro  Ser  Val  Cys  Thr
               340                      345                350

Leu  Thr  Lys  Trp  Gln  Glu  Val  Asp  Glu  Met  Leu  Arg  Ala  Glu  Tyr  Gly
          355                      360                     365

Pro  Ser  Phe  Arg  Phe  Ser  Ser  Ser  Ala  Leu  Ser  Thr  Thr  Phe  Thr  Thr
     370                      375                     380

Asn  Arg  Thr  Glu  Tyr  Ala  Leu  Ser  Arg  Val  Asp  Leu  Gly  Asp  Cys  Val
385                      390                     395                      400

Gly  Arg  Glu  Ala  Arg  Glu  Ala  Val  Asp  Arg  Ile  Phe  Leu  Arg  Arg  Tyr
               405                     410                          415

Asn  Gly  Thr  His  Val  Lys  Val  Gly  Gln  Val  Gln  Tyr  Tyr  Leu  Ala  Thr
               420                     425                     430

Ala  Gly  Phe  Leu  Ile  Ala  Tyr  Gln  Pro  Leu  Leu  Ser  Asn  Gly  Leu  Val
               435                     440                     445

Glu  Leu  Tyr  Val  Arg  Glu  Leu  Leu  Arg  Glu  Gln  Glu  Gly  Arg  Pro  Gly
     450                          455                      460

Asp  Ala  Ala  Thr  Pro  Lys  Pro  Ser  Ala  Asp  Pro  Pro  Asp  Val  Glu
465                 470                      475                      480

Arg  Ile  Lys  Thr  Thr  Ser  Ser  Val  Glu  Phe  Ala  Arg  Leu  Gln  Phe  Thr
                    485                      490                      495

Tyr  Asp  His  Ile  Gln  Arg  His  Val  Asn  Asp  Met  Leu  Gly  Arg  Ile  Ala
               500                      505                     510

Ile  Ala  Trp  Cys  Glu  Leu  Gln  Asn  His  Glu  Leu  Thr  Leu  Trp  Asn  Glu
               515                      520                     525

Ala  Arg  Lys  Leu  Asn  Pro  Asn  Ala  Ile  Ala  Ser  Ala  Thr  Val  Gly  Arg
     530                      535                     540

Arg  Val  Ser  Ala  Arg  Met  Leu  Gly  Asp  Val  Met  Ala  Val  Ser  Thr  Cys
545                      550                     555                      560

Val  Pro  Val  Thr  Pro  Asp  Asn  Val  Ile  Met  Gln  Asn  Ser  Met  Arg  Val
                    565                      570                      575

Pro  Ala  Arg  Pro  Gly  Thr  Cys  Tyr  Ser  Arg  Pro  Leu  Val  Ser  Phe  Arg
               580                     585                     590

Tyr  Glu  Glu  Gly  Gly  Pro  Leu  Val  Glu  Gly  Gln  Leu  Gly  Glu  Asp  Asn
     595                      600                     605

Glu  Ile  Arg  Leu  Glu  Arg  Asp  Ala  Leu  Glu  Pro  Cys  Thr  Val  Gly  His
     610                      615                     620

Arg  Arg  Tyr  Phe  Thr  Phe  Gly  Ala  Gly  Tyr  Val  Tyr  Phe  Glu  Asp  Tyr
625                      630                     635                      640

Ala  Tyr  Ser  His  Gln  Leu  Gly  Arg  Ala  Asp  Val  Thr  Thr  Val  Ser  Thr
               645                     650                     655

Phe  Ile  Asn  Leu  Asn  Leu  Thr  Met  Leu  Glu  Asp  His  Glu  Phe  Val  Pro
               660                     665                     670

Leu  Glu  Val  Tyr  Thr  Arg  Gln  Glu  Ile  Lys  Asp  Ser  Gly  Leu  Leu  Asp
          675                     680                     685

Tyr  Thr  Glu  Val  Gln  Arg  Arg  Asn  Gln  Leu  His  Ala  Leu  Arg  Phe  Ala
     690                      695                     700

Asp  Ile  Asp  Thr  Val  Ile  Lys  Ala  Asp  Ala  His  Ala  Pro  Leu  Phe  Ala
705                      710                     715                      720

Gly  Leu  Tyr  Ser  Phe  Phe  Glu  Gly  Leu  Gly  Asp  Val  Gly  Arg  Ala  Val
```

|       |       |       |       | 725   |       |       |       | 730   |       |       |       | 735   |       |       |
|-------|-------|-------|-------|-------|-------|-------|-------|-------|-------|-------|-------|-------|-------|-------|
| Gly   | Lys   | Val   | Val   | Met   | Gly   | Ile   | Val   | Gly   | Val   | Val   | Ser   | Ala   | Val   | Ser   |
|       |       |       | 740   |       |       |       | 745   |       |       |       | 750   |       |       |       |
| Gly   | Val   | Ser   | Ser   | Phe   | Leu   | Ser   | Asn   | Pro   | Phe   | Gly   | Ala   | Leu   | Ala   | Val   | Gly   |

Gly Val Ser Ser Phe Leu Ser Asn Pro Phe Gly Ala Leu Ala Val Gly
        755                 760                 765

Leu Leu Val Leu Ala Gly Leu Ala Ala Phe Phe Ala Phe Arg Tyr
    770                 775                 780

Val Met Arg Leu Gln Arg Asn Pro Met Lys Ala Leu Tyr Pro Leu Thr
785                 790                 795                 800

Thr Lys Glu Leu Lys Ser Asp Gly Pro Ser Arg Gly Asp Gly Gly Asp
                805                 810                 815

Gly Ala Ser Gly Gly Gly Glu Glu Asp Phe Asp Glu Ala Lys Leu Ala
            820                 825                 830

Gln Ala Arg Glu Met Ile Arg Tyr Met Ala Leu Val Ser Ala Met Glu
            835                 840                 845

Arg Thr Glu His Lys Ala Arg Lys Lys Gly Thr Ser Ala Leu Leu Ser
    850                 855                 860

Ala Lys Val Thr Asn Met Val Met Arg Lys Arg Ala Lys Pro Arg Tyr
865                 870                 875                 880

Ser Pro Leu Gly Asp Thr Asp Glu Glu Glu Leu
                885                 890

( 2 ) INFORMATION FOR SEQ ID NO:7:

( i ) SEQUENCE CHARACTERISTICS:
        ( A ) LENGTH: 2943 base pairs
        ( B ) TYPE: nucleic acid
        ( C ) STRANDEDNESS: single
        ( D ) TOPOLOGY: linear ( i i ) MOLECULE TYPE: Genomic DNA ( i x ) FEATURE:
        ( A ) NAME/KEY: CDS
        ( B ) LOCATION: 87..2744

( x i ) SEQUENCE DESCRIPTION: SEQ ID NO:7:

```
CTGCAGCACC TGGCCCCCAA GCTCGCGGCC GGCGGGCCGG AGTCGACGCC CGCGTAGTCG        60

CCCGCGTAGC GCCCGCGCGC CCCGGG ATG CGG CCT CGC GGC ACC CCC CCC TCC       113
                            Met Arg Pro Arg Gly Thr Pro Pro Ser
                              1               5

TTT CTT CCC CTC CCC GTC CTC CTC GCC CTC GCC GTG ATC GCC GCG GCC       161
Phe Leu Pro Leu Pro Val Leu Leu Ala Leu Ala Val Ile Ala Ala Ala
 10              15              20              25

GGA CGA GCC GCC CCC GCG GCG GCG GCG GCC CCG ACC GCC GAC CCC GCC       209
Gly Arg Ala Ala Pro Ala Ala Ala Ala Ala Pro Thr Ala Asp Pro Ala
             30              35              40

GCC ACG CCC GCG CTT CCC GAG GAC GAG GAG GTC CCG GAC GAG GAC GGG       257
Ala Thr Pro Ala Leu Pro Glu Asp Glu Glu Val Pro Asp Glu Asp Gly
         45              50              55

GAG GGG GTC GCC ACC CCG GCG CCC GCC GCC AAC GCG TCG GTC GAG GCC       305
Glu Gly Val Ala Thr Pro Ala Pro Ala Ala Asn Ala Ser Val Glu Ala
     60              65              70

GGC CGC GCG ACG CTG CGG GAA GAC CTG CGG GAG ATC AAG GCC CGG GAC       353
Gly Arg Ala Thr Leu Arg Glu Asp Leu Arg Glu Ile Lys Ala Arg Asp
 75              80              85

GGC GAC GCG ACC TTC TAC GTC TGC CCG CCG CCG ACC GGC GCC ACG GTG       401
Gly Asp Ala Thr Phe Tyr Val Cys Pro Pro Pro Thr Gly Ala Thr Val
 90              95             100             105

GTG CAG TTC GAG CAG CCC CGG CCG TGC CCG CGC GCG CCC GAC GGC CAG       449
```

```
Val Gln Phe Glu Gln Pro Arg Pro Cys Pro Arg Ala Pro Asp Gly Gln
            110             115                 120

AAC TAC ACG GAG GGG ATC GCG GTC GTC TTC AAG GAG AAC ATC GCC CCG        497
Asn Tyr Thr Glu Gly Ile Ala Val Val Phe Lys Glu Asn Ile Ala Pro
            125             130                 135

TAC AAG TTC AAG GCC ACC ATG TAC TAC AAG GAC GTG ACC GTC TCG CAG        545
Tyr Lys Phe Lys Ala Thr Met Tyr Tyr Lys Asp Val Thr Val Ser Gln
            140             145                 150

GTC TGG TTC GGG CAC CGG TAC TCG CAG TTC ATG GGG ATC TTC GAG GAC        593
Val Trp Phe Gly His Arg Tyr Ser Gln Phe Met Gly Ile Phe Glu Asp
            155             160                 165

CGC GCC CCC GTG CCC TTC GAG GAG GTG ATG GAC AAG ATC AAC GCC AAG        641
Arg Ala Pro Val Pro Phe Glu Glu Val Met Asp Lys Ile Asn Ala Lys
170             175             180                 185

GGG GTC TGC CGG TCG ACG GCC AAG TAC GTG CGG AAC AAC ATG GAG AGC        689
Gly Val Cys Arg Ser Thr Ala Lys Tyr Val Arg Asn Asn Met Glu Ser
                190             195                 200

ACG GCC TTC CAC CGC GAC GAC CAC GAG TCG GAC ATG GCG CTG AAG CCG        737
Thr Ala Phe His Arg Asp Asp His Glu Ser Asp Met Ala Leu Lys Pro
                205             210                 215

GCC AAG GCC GCG ACC CGC ACC AGC CGC GGC TGG CAC ACC ACC GAC CTC        785
Ala Lys Ala Ala Thr Arg Thr Ser Arg Gly Trp His Thr Thr Asp Leu
            220             225                 230

AAG TAC AAC CCC GCG CGG GTC GAG GCC TTC CAC CGC TAC GGC ACC ACG        833
Lys Tyr Asn Pro Ala Arg Val Glu Ala Phe His Arg Tyr Gly Thr Thr
            235             240                 245

GTG AAC TGT ATC GTC GAG GAG GTG GAG GCC CGC TCG GTG TAC CCG TAC        881
Val Asn Cys Ile Val Glu Glu Val Glu Ala Arg Ser Val Tyr Pro Tyr
250             255             260                 265

GAC GAG TTC GTG CTG GCG ACC GGG GAC TTT GTG TAC ATG TCG CCG TTC        929
Asp Glu Phe Val Leu Ala Thr Gly Asp Phe Val Tyr Met Ser Pro Phe
                270             275                 280

TAC GGC TAC CGC GAC GGG TCC CAC GGG GAG CAC ACG GCC TAC GCC GCG        977
Tyr Gly Tyr Arg Asp Gly Ser His Gly Glu His Thr Ala Tyr Ala Ala
                285             290                 295

GAC CGC TTC CGG CAG GTC GAC GGC TAC TAC GAG CGC GAC CTC TCG ACG       1025
Asp Arg Phe Arg Gln Val Asp Gly Tyr Tyr Glu Arg Asp Leu Ser Thr
            300             305                 310

GGC CGC CGC GCC GCC GCG CCG GTG ACG CGC AAC CTG CTG ACC ACC CCC       1073
Gly Arg Arg Ala Ala Ala Pro Val Thr Arg Asn Leu Leu Thr Thr Pro
315             320                 325

AAG TTC ACC GTG GGC TGG GAC TGG GCC CCC AAG CGC CCC TCG GTC TGC       1121
Lys Phe Thr Val Gly Trp Asp Trp Ala Pro Lys Arg Pro Ser Val Cys
330             335                 340             345

ACG CTG ACC AAG TGG CGG GAG GTG GAC GAG ATG CTG CGC GCC GAG TAC       1169
Thr Leu Thr Lys Trp Arg Glu Val Asp Glu Met Leu Arg Ala Glu Tyr
            350             355                 360

GGC CCC TCG TTC CGC TTC TCC TCG GCC GCC CTC TCG ACC ACC TTC ACC       1217
Gly Pro Ser Phe Arg Phe Ser Ser Ala Ala Leu Ser Thr Thr Phe Thr
            365             370                 375

GCC AAC CGC ACC GAG TAC GCC CTG TCG CGC GTC GAC CTC GCG GAC TGC       1265
Ala Asn Arg Thr Glu Tyr Ala Leu Ser Arg Val Asp Leu Ala Asp Cys
            380             385                 390

GTC GGG CGC GAG GCC CGC GAG GCC GTG GAC CGC ATC TTC CTC CGG CGC       1313
Val Gly Arg Glu Ala Arg Glu Ala Val Asp Arg Ile Phe Leu Arg Arg
            395             400                 405

TAC AAC GGG ACG CAC GTG AAG GTG GGC CAG GTG CAG TAC TAC CTG GCC       1361
Tyr Asn Gly Thr His Val Lys Val Gly Gln Val Gln Tyr Tyr Leu Ala
410             415             420                 425

ACG GGC GGC TTC CTC ATC GCG TAC CAG CCC CTC CTC AGC AAC GCG CTC       1409
```

|  |  |  |  |  |  |  |  |  |  |  |  |  |  |  |  |
|---|---|---|---|---|---|---|---|---|---|---|---|---|---|---|---|
| Thr | Gly | Gly | Phe | Leu | Ile | Ala | Tyr | Gln | Pro | Leu | Leu | Ser | Asn | Ala | Leu |
|  |  |  |  | 430 |  |  |  | 435 |  |  |  |  |  | 440 |  |

| GTG | GAG | CTC | TAC | GTG | CGG | GAG | CTC | GTC | CGC | GAG | CAG | ACG | CGG | CGG | CCG | 1457 |
|---|---|---|---|---|---|---|---|---|---|---|---|---|---|---|---|---|
| Val | Glu | Leu | Tyr | Val | Arg | Glu | Leu | Val | Arg | Glu | Gln | Thr | Arg | Arg | Pro |  |
|  |  |  | 445 |  |  |  | 450 |  |  |  |  | 455 |  |  |  |  |

| GCC | GGG | GGC | GAC | CCC | GGG | GAG | GCG | GCC | ACC | CCG | GGC | CCC | TCC | GTG | GAC | 1505 |
|---|---|---|---|---|---|---|---|---|---|---|---|---|---|---|---|---|
| Ala | Gly | Gly | Asp | Pro | Gly | Glu | Ala | Ala | Thr | Pro | Gly | Pro | Ser | Val | Asp |  |
|  |  | 460 |  |  |  | 465 |  |  |  |  | 470 |  |  |  |  |  |

| CCC | CCC | AGC | GTG | GAG | CGC | ATC | AAG | ACC | ACG | TCC | TCG | GTC | GAG | TTC | GCG | 1553 |
|---|---|---|---|---|---|---|---|---|---|---|---|---|---|---|---|---|
| Pro | Pro | Ser | Val | Glu | Arg | Ile | Lys | Thr | Thr | Ser | Ser | Val | Glu | Phe | Ala |  |
| 475 |  |  |  |  | 480 |  |  |  |  | 485 |  |  |  |  |  |  |

| CGC | CTG | CAG | TTC | ACG | TAC | GAC | CAC | ATC | CAG | CGC | CAC | GTC | AAC | GAC | ATG | 1601 |
|---|---|---|---|---|---|---|---|---|---|---|---|---|---|---|---|---|
| Arg | Leu | Gln | Phe | Thr | Tyr | Asp | His | Ile | Gln | Arg | His | Val | Asn | Asp | Met |  |
| 490 |  |  |  | 495 |  |  |  |  | 500 |  |  |  |  | 505 |  |  |

| CTG | GGG | CGC | ATC | GCC | ATC | GCC | TGG | TGC | GAG | CTG | CAG | AAC | CGC | GAG | CTG | 1649 |
|---|---|---|---|---|---|---|---|---|---|---|---|---|---|---|---|---|
| Leu | Gly | Arg | Ile | Ala | Ile | Ala | Trp | Cys | Glu | Leu | Gln | Asn | Arg | Glu | Leu |  |
|  |  |  |  | 510 |  |  |  | 515 |  |  |  |  | 520 |  |  |  |

| ACG | CTG | TGG | AAC | GAG | GCC | CGC | CGG | CTG | AAC | CCC | GGG | GCC | ATC | GCC | TCG | 1697 |
|---|---|---|---|---|---|---|---|---|---|---|---|---|---|---|---|---|
| Thr | Leu | Trp | Asn | Glu | Ala | Arg | Arg | Leu | Asn | Pro | Gly | Ala | Ile | Ala | Ser |  |
|  |  |  | 525 |  |  |  |  | 530 |  |  |  |  | 535 |  |  |  |

| GCC | ACC | GTG | GGC | CGC | CGG | GTG | AGC | GCG | CGC | ATG | CTC | GGG | GAC | GTC | ATG | 1745 |
|---|---|---|---|---|---|---|---|---|---|---|---|---|---|---|---|---|
| Ala | Thr | Val | Gly | Arg | Arg | Val | Ser | Ala | Arg | Met | Leu | Gly | Asp | Val | Met |  |
|  |  | 540 |  |  |  |  | 545 |  |  |  |  | 550 |  |  |  |  |

| GCC | GTC | TCG | ACC | TGC | GTG | CCC | GTG | GCC | CCC | GAC | AAC | GTC | ATC | ATG | CAG | 1793 |
|---|---|---|---|---|---|---|---|---|---|---|---|---|---|---|---|---|
| Ala | Val | Ser | Thr | Cys | Val | Pro | Val | Ala | Pro | Asp | Asn | Val | Ile | Met | Gln |  |
|  | 555 |  |  |  |  | 560 |  |  |  |  | 565 |  |  |  |  |  |

| AAC | TCG | ATG | CGC | GTG | GCC | GCG | CGC | CCC | GGG | ACG | TGC | TAC | AGC | CGC | CCC | 1841 |
|---|---|---|---|---|---|---|---|---|---|---|---|---|---|---|---|---|
| Asn | Ser | Met | Arg | Val | Ala | Ala | Arg | Pro | Gly | Thr | Cys | Tyr | Ser | Arg | Pro |  |
| 570 |  |  |  | 575 |  |  |  |  | 580 |  |  |  |  | 585 |  |  |

| CTG | GTC | AGC | TTC | CGC | TAC | GAG | GCC | GAC | GGG | CCC | CTC | GTC | GAG | GGC | CAG | 1889 |
|---|---|---|---|---|---|---|---|---|---|---|---|---|---|---|---|---|
| Leu | Val | Ser | Phe | Arg | Tyr | Glu | Ala | Asp | Gly | Pro | Leu | Val | Glu | Gly | Gln |  |
|  |  |  |  | 590 |  |  |  | 595 |  |  |  |  | 600 |  |  |  |

| CTG | GGC | GAG | GAC | AAC | GAG | ATC | CGC | CTC | GAG | CGC | GAC | GCC | CTG | GAG | CCC | 1937 |
|---|---|---|---|---|---|---|---|---|---|---|---|---|---|---|---|---|
| Leu | Gly | Glu | Asp | Asn | Glu | Ile | Arg | Leu | Glu | Arg | Asp | Ala | Leu | Glu | Pro |  |
|  |  |  | 605 |  |  |  |  | 610 |  |  |  |  | 615 |  |  |  |

| TGC | ACC | GTC | GGC | CAC | CGC | CGG | TAC | TTC | ACC | TTC | GGG | GCG | GGC | TAC | GTG | 1985 |
|---|---|---|---|---|---|---|---|---|---|---|---|---|---|---|---|---|
| Cys | Thr | Val | Gly | His | Arg | Arg | Tyr | Phe | Thr | Phe | Gly | Ala | Gly | Tyr | Val |  |
|  |  | 620 |  |  |  |  | 625 |  |  |  |  | 630 |  |  |  |  |

| TAC | TTT | GAG | GAG | TAC | GCC | TAC | TCC | CAT | CAG | CTG | GGC | CGC | GCC | GAC | GTG | 2033 |
|---|---|---|---|---|---|---|---|---|---|---|---|---|---|---|---|---|
| Tyr | Phe | Glu | Glu | Tyr | Ala | Tyr | Ser | His | Gln | Leu | Gly | Arg | Ala | Asp | Val |  |
| 635 |  |  |  |  | 640 |  |  |  |  | 645 |  |  |  |  |  |  |

| ACG | ACC | GTT | AGC | ACG | TTC | ATC | AAC | CTC | AAC | CTC | ACG | ATG | CTC | GAG | GAC | 2081 |
|---|---|---|---|---|---|---|---|---|---|---|---|---|---|---|---|---|
| Thr | Thr | Val | Ser | Thr | Phe | Ile | Asn | Leu | Asn | Leu | Thr | Met | Leu | Glu | Asp |  |
| 650 |  |  |  |  | 655 |  |  |  |  | 660 |  |  |  |  | 665 |  |

| CAC | GAG | TTC | GTG | CCC | CTG | GAG | GTG | TAC | ACC | CGC | CAG | GAG | ATC | AAG | GAC | 2129 |
|---|---|---|---|---|---|---|---|---|---|---|---|---|---|---|---|---|
| His | Glu | Phe | Val | Pro | Leu | Glu | Val | Tyr | Thr | Arg | Gln | Glu | Ile | Lys | Asp |  |
|  |  |  |  | 670 |  |  |  |  | 675 |  |  |  |  | 680 |  |  |

| AGC | GGC | CTG | CTG | GAC | TAC | ACC | GAG | GTC | CAG | CGC | CGC | AAC | CAG | CTC | CAC | 2177 |
|---|---|---|---|---|---|---|---|---|---|---|---|---|---|---|---|---|
| Ser | Gly | Leu | Leu | Asp | Tyr | Thr | Glu | Val | Gln | Arg | Arg | Asn | Gln | Leu | His |  |
|  |  |  |  | 685 |  |  |  |  | 690 |  |  |  |  | 695 |  |  |

| GCG | CTC | CGC | TTC | GCC | GAC | ATC | GAC | ACG | GTC | ATC | AAG | GCC | GAC | GCA | CAC | 2225 |
|---|---|---|---|---|---|---|---|---|---|---|---|---|---|---|---|---|
| Ala | Leu | Arg | Phe | Ala | Asp | Ile | Asp | Thr | Val | Ile | Lys | Ala | Asp | Ala | His |  |
|  |  | 700 |  |  |  |  | 705 |  |  |  |  | 710 |  |  |  |  |

| GCC | GCC | CTC | TTC | GCG | GGC | CTC | TAC | TCC | TTC | TTC | GAG | GGC | CTC | GGG | GAC | 2273 |
|---|---|---|---|---|---|---|---|---|---|---|---|---|---|---|---|---|
| Ala | Ala | Leu | Phe | Ala | Gly | Leu | Tyr | Ser | Phe | Phe | Glu | Gly | Leu | Gly | Asp |  |
|  |  | 715 |  |  |  |  | 720 |  |  |  |  | 725 |  |  |  |  |

| GTG | GGC | CGC | GCG | GTC | GGA | AAG | GTC | GTC | ATG | GGC | ATC | GTG | GGC | GGG | GTC | 2321 |
|---|---|---|---|---|---|---|---|---|---|---|---|---|---|---|---|---|
| Val | Gly | Arg | Ala | Val | Gly | Lys | Val | Val | Met | Gly | Ile | Val | Gly | Gly | Val |  |
| 730 |  |  |  |  | 735 |  |  |  |  | 740 |  |  |  |  | 745 |  |

| GTC | TCC | GCC | GTC | TCG | GGC | GTG | TCC | TCG | TTC | CTC | TCC | AAC | CCC | TTC | GGG | 2369 |
|---|---|---|---|---|---|---|---|---|---|---|---|---|---|---|---|---|

|     |     |     |     |     |     |     |     |     |     |     |     |     |     |     |     |     |
|---|---|---|---|---|---|---|---|---|---|---|---|---|---|---|---|---|
| Val | Ser | Ala | Val | Ser | Gly | Val | Ser | Ser | Phe | Leu | Ser | Asn | Pro | Phe | Gly |  |
|     |     |     |     | 750 |     |     |     | 755 |     |     |     |     | 760 |     |     |  |
| GCC | CTG | GCC | GTG | GGG | CTG | CTG | GTC | CTG | GCG | GGG | CTG | GCG | GCC | GCC | TTC | 2417 |
| Ala | Leu | Ala | Val | Gly | Leu | Leu | Val | Leu | Ala | Gly | Leu | Ala | Ala | Ala | Phe |  |
|     |     |     |     | 765 |     |     |     | 770 |     |     |     |     | 775 |     |     |  |
| TTC | GCC | TTC | CGC | TAC | GTC | ATG | CGC | CTG | CAG | CGG | AAC | CCC | ATG | AAG | GCC | 2465 |
| Phe | Ala | Phe | Arg | Tyr | Val | Met | Arg | Leu | Gln | Arg | Asn | Pro | Met | Lys | Ala |  |
|     |     | 780 |     |     |     |     | 785 |     |     |     |     | 790 |     |     |     |  |
| CTG | TAC | CCG | CTG | ACC | ACC | AAG | GAG | CTC | AAG | AGC | GAC | GGC | GCG | CCG | CTG | 2513 |
| Leu | Tyr | Pro | Leu | Thr | Thr | Lys | Glu | Leu | Lys | Ser | Asp | Gly | Ala | Pro | Leu |  |
|     | 795 |     |     |     |     | 800 |     |     |     |     | 805 |     |     |     |     |  |
| GCG | GGC | GGC | GGC | GAG | GAC | GGC | GCG | GAG | GAC | TTT | GAC | GAG | GCC | AAG | CTG | 2561 |
| Ala | Gly | Gly | Gly | Glu | Asp | Gly | Ala | Glu | Asp | Phe | Asp | Glu | Ala | Lys | Leu |  |
| 810 |     |     |     |     | 815 |     |     |     |     | 820 |     |     |     |     | 825 |  |
| GCG | CAG | GCG | CGG | GAG | ATG | ATC | CGC | TAC | ATG | GCC | CTG | GTC | TCG | GCC | ATG | 2609 |
| Ala | Gln | Ala | Arg | Glu | Met | Ile | Arg | Tyr | Met | Ala | Leu | Val | Ser | Ala | Met |  |
|     |     |     |     | 830 |     |     |     |     | 835 |     |     |     |     | 840 |     |  |
| GAG | CGC | ACC | GAG | CAC | AAG | GCC | CGC | AAG | AAG | GGC | ACG | AGC | GCC | CTG | CTG | 2657 |
| Glu | Arg | Thr | Glu | His | Lys | Ala | Arg | Lys | Lys | Gly | Thr | Ser | Ala | Leu | Leu |  |
|     |     |     |     | 845 |     |     |     |     | 850 |     |     |     |     | 855 |     |  |
| AGC | GCG | AAG | GTT | ACC | GAC | GCG | GTG | ATG | CGA | AAG | CGC | GCC | CGG | CCC | CGG | 2705 |
| Ser | Ala | Lys | Val | Thr | Asp | Ala | Val | Met | Arg | Lys | Arg | Ala | Arg | Pro | Arg |  |
|     |     | 860 |     |     |     |     | 865 |     |     |     |     | 870 |     |     |     |  |
| TAC | TCT | CCC | CTC | CGC | GAC | ACG | GAC | GAG | GAG | GAA | CTG | TAGCGGCCCG |  |  |  | 2751 |
| Tyr | Ser | Pro | Leu | Arg | Asp | Thr | Asp | Glu | Glu | Glu | Leu |     |     |     |     |  |
|     | 875 |     |     |     |     | 880 |     |     |     |     | 885 |     |     |     |     |  |

| | |
|---|---|
| AGCGGACCCG ACCCCGACCC CAGAGAATGC TCAATAAACT ATGACAAAAA ACACACGCGG | 2811 |
| TGTGATCGGT GACGGATCGT TTGTGCGTCG GAAGCGCGCG GCGGCTTCG GTCCCACGGG | 2871 |
| GCTACCCCGC CCGGGGGGGA TCTGGTAGGG CAGACCCCAT CCCACCCCCT CCCCCGGGGG | 2931 |
| AGGGGGACAG AA | 2943 |

( 2 ) INFORMATION FOR SEQ ID NO:8:

( i ) SEQUENCE CHARACTERISTICS:
        ( A ) LENGTH: 885 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

|     |     |     |     |     |     |     |     |     |     |     |     |     |     |     |     |
|---|---|---|---|---|---|---|---|---|---|---|---|---|---|---|---|
| Met | Arg | Pro | Arg | Gly | Thr | Pro | Pro | Ser | Phe | Leu | Pro | Leu | Pro | Val | Leu |
| 1 |     |     |     | 5 |     |     |     |     | 10 |     |     |     |     | 15 |     |
| Leu | Ala | Leu | Ala | Val | Ile | Ala | Ala | Ala | Gly | Arg | Ala | Ala | Pro | Ala | Ala |
|     |     |     |     | 20 |     |     |     |     | 25 |     |     |     |     | 30 |     |
| Ala | Ala | Ala | Pro | Thr | Ala | Asp | Pro | Ala | Ala | Thr | Pro | Ala | Leu | Pro | Glu |
|     |     | 35 |     |     |     |     | 40 |     |     |     |     | 45 |     |     |     |
| Asp | Glu | Glu | Val | Pro | Asp | Glu | Asp | Gly | Glu | Gly | Val | Ala | Thr | Pro | Ala |
|     | 50 |     |     |     |     | 55 |     |     |     |     | 60 |     |     |     |     |
| Pro | Ala | Ala | Asn | Ala | Ser | Val | Glu | Ala | Gly | Arg | Ala | Thr | Leu | Arg | Glu |
| 65 |     |     |     |     | 70 |     |     |     |     | 75 |     |     |     |     | 80 |
| Asp | Leu | Arg | Glu | Ile | Lys | Ala | Arg | Asp | Gly | Asp | Ala | Thr | Phe | Tyr | Val |
|     |     |     |     | 85 |     |     |     |     | 90 |     |     |     |     | 95 |     |
| Cys | Pro | Pro | Pro | Thr | Gly | Ala | Thr | Val | Val | Gln | Phe | Glu | Gln | Pro | Arg |
|     |     |     |     | 100 |     |     |     |     | 105 |     |     |     |     | 110 |     |
| Pro | Cys | Pro | Arg | Ala | Pro | Asp | Gly | Gln | Asn | Tyr | Thr | Glu | Gly | Ile | Ala |
|     |     |     | 115 |     |     |     |     | 120 |     |     |     |     | 125 |     |     |
| Val | Val | Phe | Lys | Glu | Asn | Ile | Ala | Pro | Tyr | Lys | Phe | Lys | Ala | Thr | Met |

|     |     |     |     |     | 130 |     |     |     |     | 135 |     |     |     |     | 140 |     |     |
| --- | --- | --- | --- | --- | --- | --- | --- | --- | --- | --- | --- | --- | --- | --- | --- | --- | --- |
| Tyr | Tyr | Lys | Asp | Val | Thr | Val | Ser | Gln | Val | Trp | Phe | Gly | His | Arg | Tyr |
| 145 |     |     |     |     | 150 |     |     |     |     | 155 |     |     |     |     | 160 |
| Ser | Gln | Phe | Met | Gly | Ile | Phe | Glu | Asp | Arg | Ala | Pro | Val | Pro | Phe | Glu |
|     |     |     |     | 165 |     |     |     |     | 170 |     |     |     |     | 175 |     |
| Glu | Val | Met | Asp | Lys | Ile | Asn | Ala | Lys | Gly | Val | Cys | Arg | Ser | Thr | Ala |
|     |     |     | 180 |     |     |     |     | 185 |     |     |     |     | 190 |     |     |
| Lys | Tyr | Val | Arg | Asn | Asn | Met | Glu | Ser | Thr | Ala | Phe | His | Arg | Asp | Asp |
|     |     | 195 |     |     |     |     | 200 |     |     |     |     |     | 205 |     |     |
| His | Glu | Ser | Asp | Met | Ala | Leu | Lys | Pro | Ala | Lys | Ala | Thr | Arg | Thr |
|     | 210 |     |     |     |     | 215 |     |     |     |     | 220 |     |     |     |
| Ser | Arg | Gly | Trp | His | Thr | Thr | Asp | Leu | Lys | Tyr | Asn | Pro | Ala | Arg | Val |
| 225 |     |     |     |     | 230 |     |     |     |     | 235 |     |     |     |     | 240 |
| Glu | Ala | Phe | His | Arg | Tyr | Gly | Thr | Thr | Val | Asn | Cys | Ile | Val | Glu | Glu |
|     |     |     |     | 245 |     |     |     |     | 250 |     |     |     |     | 255 |     |
| Val | Glu | Ala | Arg | Ser | Val | Tyr | Pro | Tyr | Asp | Glu | Phe | Val | Leu | Ala | Thr |
|     |     |     | 260 |     |     |     |     | 265 |     |     |     |     | 270 |     |     |
| Gly | Asp | Phe | Val | Tyr | Met | Ser | Pro | Phe | Tyr | Gly | Tyr | Arg | Asp | Gly | Ser |
|     |     | 275 |     |     |     |     | 280 |     |     |     |     |     | 285 |     |     |
| His | Gly | Glu | His | Thr | Ala | Tyr | Ala | Ala | Asp | Arg | Phe | Arg | Gln | Val | Asp |
|     | 290 |     |     |     |     | 295 |     |     |     |     | 300 |     |     |     |     |
| Gly | Tyr | Tyr | Glu | Arg | Asp | Leu | Ser | Thr | Gly | Arg | Arg | Ala | Ala | Ala | Pro |
| 305 |     |     |     |     | 310 |     |     |     |     | 315 |     |     |     |     | 320 |
| Val | Thr | Arg | Asn | Leu | Leu | Thr | Thr | Pro | Lys | Phe | Thr | Val | Gly | Trp | Asp |
|     |     |     |     | 325 |     |     |     |     | 330 |     |     |     |     | 335 |     |
| Trp | Ala | Pro | Lys | Arg | Pro | Ser | Val | Cys | Thr | Leu | Thr | Lys | Trp | Arg | Glu |
|     |     |     | 340 |     |     |     |     | 345 |     |     |     |     | 350 |     |     |
| Val | Asp | Glu | Met | Leu | Arg | Ala | Glu | Tyr | Gly | Pro | Ser | Phe | Arg | Phe | Ser |
|     |     |     | 355 |     |     |     |     | 360 |     |     |     |     | 365 |     |     |
| Ser | Ala | Ala | Leu | Ser | Thr | Thr | Phe | Thr | Ala | Asn | Arg | Thr | Glu | Tyr | Ala |
|     | 370 |     |     |     |     | 375 |     |     |     |     | 380 |     |     |     |     |
| Leu | Ser | Arg | Val | Asp | Leu | Ala | Asp | Cys | Val | Gly | Arg | Glu | Ala | Arg | Glu |
| 385 |     |     |     |     | 390 |     |     |     |     | 395 |     |     |     |     | 400 |
| Ala | Val | Asp | Arg | Ile | Phe | Leu | Arg | Arg | Tyr | Asn | Gly | Thr | His | Val | Lys |
|     |     |     |     | 405 |     |     |     |     | 410 |     |     |     |     | 415 |     |
| Val | Gly | Gln | Val | Gln | Tyr | Tyr | Leu | Ala | Thr | Gly | Gly | Phe | Leu | Ile | Ala |
|     |     |     | 420 |     |     |     |     | 425 |     |     |     |     | 430 |     |     |
| Tyr | Gln | Pro | Leu | Leu | Ser | Asn | Ala | Leu | Val | Glu | Leu | Tyr | Val | Arg | Glu |
|     |     | 435 |     |     |     |     | 440 |     |     |     |     |     | 445 |     |     |
| Leu | Val | Arg | Glu | Gln | Thr | Arg | Arg | Pro | Ala | Gly | Gly | Asp | Pro | Gly | Glu |
|     | 450 |     |     |     |     | 455 |     |     |     |     | 460 |     |     |     |     |
| Ala | Ala | Thr | Pro | Gly | Pro | Ser | Val | Asp | Pro | Pro | Ser | Val | Glu | Arg | Ile |
| 465 |     |     |     |     | 470 |     |     |     |     | 475 |     |     |     |     | 480 |
| Lys | Thr | Thr | Ser | Ser | Val | Glu | Phe | Ala | Arg | Leu | Gln | Phe | Thr | Tyr | Asp |
|     |     |     |     | 485 |     |     |     |     | 490 |     |     |     |     | 495 |     |
| His | Ile | Gln | Arg | His | Val | Asn | Asp | Met | Leu | Gly | Arg | Ile | Ala | Ile | Ala |
|     |     |     | 500 |     |     |     |     | 505 |     |     |     |     | 510 |     |     |
| Trp | Cys | Glu | Leu | Gln | Asn | Arg | Glu | Leu | Thr | Leu | Trp | Asn | Glu | Ala | Arg |
|     |     | 515 |     |     |     |     | 520 |     |     |     |     |     | 525 |     |     |
| Arg | Leu | Asn | Pro | Gly | Ala | Ile | Ala | Ser | Ala | Thr | Val | Gly | Arg | Arg | Val |
|     | 530 |     |     |     |     | 535 |     |     |     |     | 540 |     |     |     |     |
| Ser | Ala | Arg | Met | Leu | Gly | Asp | Val | Met | Ala | Val | Ser | Thr | Cys | Val | Pro |
| 545 |     |     |     |     | 550 |     |     |     |     | 555 |     |     |     |     | 560 |

| | | | | | | | | | | | | | | |
|---|---|---|---|---|---|---|---|---|---|---|---|---|---|---|
| Val | Ala | Pro | Asp | Asn | Val | Ile | Met | Gln | Asn | Ser | Met | Arg | Val | Ala | Ala |
| | | | | 565 | | | | 570 | | | | | 575 | | |
| Arg | Pro | Gly | Thr | Cys | Tyr | Ser | Arg | Pro | Leu | Val | Ser | Phe | Arg | Tyr | Glu |
| | | | 580 | | | | | 585 | | | | | 590 | | |
| Ala | Asp | Gly | Pro | Leu | Val | Glu | Gly | Gln | Leu | Gly | Glu | Asp | Asn | Glu | Ile |
| | | 595 | | | | | 600 | | | | | 605 | | | |
| Arg | Leu | Glu | Arg | Asp | Ala | Leu | Glu | Pro | Cys | Thr | Val | Gly | His | Arg | Arg |
| | 610 | | | | | 615 | | | | | 620 | | | | |
| Tyr | Phe | Thr | Phe | Gly | Ala | Gly | Tyr | Val | Tyr | Phe | Glu | Glu | Tyr | Ala | Tyr |
| 625 | | | | | 630 | | | | | 635 | | | | | 640 |
| Ser | His | Gln | Leu | Gly | Arg | Ala | Asp | Val | Thr | Thr | Val | Ser | Thr | Phe | Ile |
| | | | | 645 | | | | | 650 | | | | | 655 | |
| Asn | Leu | Asn | Leu | Thr | Met | Leu | Glu | Asp | His | Glu | Phe | Val | Pro | Leu | Glu |
| | | | 660 | | | | | 665 | | | | | 670 | | |
| Val | Tyr | Thr | Arg | Gln | Glu | Ile | Lys | Asp | Ser | Gly | Leu | Leu | Asp | Tyr | Thr |
| | | 675 | | | | | 680 | | | | | 685 | | | |
| Glu | Val | Gln | Arg | Arg | Asn | Gln | Leu | His | Ala | Leu | Arg | Phe | Ala | Asp | Ile |
| | 690 | | | | | 695 | | | | | 700 | | | | |
| Asp | Thr | Val | Ile | Lys | Ala | Asp | Ala | His | Ala | Ala | Leu | Phe | Ala | Gly | Leu |
| 705 | | | | | 710 | | | | | 715 | | | | | 720 |
| Tyr | Ser | Phe | Phe | Glu | Gly | Leu | Gly | Asp | Val | Gly | Arg | Ala | Val | Gly | Lys |
| | | | | 725 | | | | | 730 | | | | | 735 | |
| Val | Val | Met | Gly | Ile | Val | Gly | Gly | Val | Val | Ser | Ala | Val | Ser | Gly | Val |
| | | | 740 | | | | | 745 | | | | | 750 | | |
| Ser | Ser | Phe | Leu | Ser | Asn | Pro | Phe | Gly | Ala | Leu | Ala | Val | Gly | Leu | Leu |
| | | 755 | | | | | 760 | | | | | 765 | | | |
| Val | Leu | Ala | Gly | Leu | Ala | Ala | Ala | Phe | Phe | Ala | Phe | Arg | Tyr | Val | Met |
| | 770 | | | | | 775 | | | | | 780 | | | | |
| Arg | Leu | Gln | Arg | Asn | Pro | Met | Lys | Ala | Leu | Tyr | Pro | Leu | Thr | Thr | Lys |
| 785 | | | | | 790 | | | | | 795 | | | | | 800 |
| Glu | Leu | Lys | Ser | Asp | Gly | Ala | Pro | Leu | Ala | Gly | Gly | Gly | Glu | Asp | Gly |
| | | | | 805 | | | | | 810 | | | | | 815 | |
| Ala | Glu | Asp | Phe | Asp | Glu | Ala | Lys | Leu | Ala | Gln | Ala | Arg | Glu | Met | Ile |
| | | | 820 | | | | | 825 | | | | | 830 | | |
| Arg | Tyr | Met | Ala | Leu | Val | Ser | Ala | Met | Glu | Arg | Thr | Glu | His | Lys | Ala |
| | | 835 | | | | | 840 | | | | | 845 | | | |
| Arg | Lys | Lys | Gly | Thr | Ser | Ala | Leu | Leu | Ser | Ala | Lys | Val | Thr | Asp | Ala |
| | 850 | | | | | 855 | | | | | 860 | | | | |
| Val | Met | Arg | Lys | Arg | Ala | Arg | Pro | Arg | Tyr | Ser | Pro | Leu | Arg | Asp | Thr |
| 865 | | | | | 870 | | | | | 875 | | | | | 880 |
| Asp | Glu | Glu | Glu | Leu | | | | | | | | | | | |
| | | | | 885 | | | | | | | | | | | |

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:9:

TTCACCGTGG CCTGGGACTG G        21

( 2 ) INFORMATION FOR SEQ ID NO:10:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: Genomic DNA ( x i ) SEQUENCE DESCRIPTION: SEQ ID NO:10:

GCGATTCTGC AGCTCGCACC A 21

( 2 ) INFORMATION FOR SEQ ID NO:11:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: Genomic DNA ( x i ) SEQUENCE DESCRIPTION: SEQ ID NO:11:

TTCACCGTGG GCTGGGACTG G 21

( 2 ) INFORMATION FOR SEQ ID NO:12:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: Genomic DNA ( x i ) SEQUENCE DESCRIPTION: SEQ ID NO:12:

GCGGTTCTGG AGCTCGCACC A 21